United States Patent
Breitenbach et al.

(10) Patent No.: US 7,989,654 B2
(45) Date of Patent: *Aug. 2, 2011

(54) HIGH PURITY BASES OF 3,3-DIPHENYLPROPYLAMINO MONOESTERS

(75) Inventors: Armin Breitenbach, Monheim (DE); Claus Meese, Monheim (DE); Hans-Michael Wolff, Monheim (DE); Roland Drews, Monheim (DE)

(73) Assignee: UCB Pharma GmbH, Monheim (DE)

( * ) Notice: Subject to any disclaimer, the term of this patent is extended or adjusted under 35 U.S.C. 154(b) by 0 days.

This patent is subject to a terminal disclaimer.

(21) Appl. No.: 12/141,489

(22) Filed: Jun. 18, 2008

(65) Prior Publication Data

US 2009/0012159 A1 Jan. 8, 2009

Related U.S. Application Data

(62) Division of application No. 10/532,836, filed as application No. PCT/EP2004/003567 on Apr. 3, 2004.

(30) Foreign Application Priority Data

Apr. 8, 2003 (DE) ................................ 103 15 917

(51) Int. Cl.
C07C 69/017 (2006.01)
(52) U.S. Cl. ...................................................... 560/140
(58) Field of Classification Search .................. None
See application file for complete search history.

(56) References Cited

U.S. PATENT DOCUMENTS

| | | | |
|---|---|---|---|
| 2,556,636 A | 6/1951 | Sperber et al. | |
| 2,567,245 A | 9/1951 | Sperber et al. | |
| 2,676,964 A | 4/1954 | Sperber et al. | |
| 3,261,841 A | 7/1966 | Zenitz | |
| 3,446,901 A | 5/1969 | Macclesfield | |
| 4,675,009 A * | 6/1987 | Hymes et al. | 604/304 |
| 4,988,730 A | 1/1991 | Korbonits et al. | |
| 5,271,940 A * | 12/1993 | Cleary et al. | 424/448 |
| 5,382,600 A | 1/1995 | Jonsson et al. | |
| 5,559,269 A | 9/1996 | Johansson et al. | |
| 5,922,914 A | 7/1999 | Gage et al. | |
| 6,310,248 B2 | 10/2001 | Andersson et al. | |
| 6,517,864 B1 | 2/2003 | Jacobsen et al. | |
| 6,566,537 B2 | 5/2003 | Andersson et al. | |
| 6,630,162 B1 | 10/2003 | Nilvebrant et al. | |
| 6,689,916 B2 | 2/2004 | Andersson et al. | |
| 6,713,464 B1 | 3/2004 | Meese et al. | |
| 6,770,295 B1 | 8/2004 | Kreilgard et al. | |
| 6,783,769 B1 | 8/2004 | Arth et al. | |
| 6,809,214 B2 | 10/2004 | Meese | |
| 6,809,225 B2 | 10/2004 | Donsbach et al. | |
| 6,858,650 B1 | 2/2005 | Meese | |
| 6,890,920 B2 | 5/2005 | Richards et al. | |
| 6,911,217 B1 | 6/2005 | Gren et al. | |
| 6,936,718 B2 | 8/2005 | Chen et al. | |
| 7,008,637 B2 | 3/2006 | Jacobsen et al. | |
| 7,230,030 B2 | 6/2007 | Meese et al. | |
| 7,670,621 B2 * | 3/2010 | Breitenbach et al. | 424/486 |
| 2003/0152624 A1 | 8/2003 | Aldrich et al. | |
| 2004/0064821 A1 | 4/2004 | Rousselle | |
| 2005/0004223 A1 | 1/2005 | Slatter et al. | |

FOREIGN PATENT DOCUMENTS

| | | | |
|---|---|---|---|
| DE | 830193 | | 2/1952 |
| DE | 766207 | | 12/1952 |
| DE | 925468 | * | 3/1955 |
| DE | 1216318 | * | 5/1966 |
| EP | 325571 | * | 7/1989 |
| EP | 667852 | * | 8/1995 |
| EP | 948321 | | 12/1997 |
| EP | 831799 | | 4/1998 |
| EP | 872233 | | 10/1998 |
| EP | 957073 | | 11/1999 |
| EP | 1019358 | | 7/2000 |
| EP | 1128819 | * | 9/2001 |

(Continued)

OTHER PUBLICATIONS

Berge et al. Journal of Pharmaceutical Sciences, 1977, vol. 66, pp. 1-19.*

(Continued)

*Primary Examiner* — Daniel M Sullivan
*Assistant Examiner* — Yevegeny Valenrod
(74) *Attorney, Agent, or Firm* — Kenyon & Kenyon LLP

(57) ABSTRACT

The invention relates to a compound of general formula (I) wherein A represents deuterium or hydrogen, R represents a group selected from $C_{1-6}$ alkyl, $C_{3-10}$ cycloalkyl or phenyl, which can be substituted by C1-3 alkoxy, fluorine, chlorine, bromine, iodine, nitro, amino, hydroxyl, oxo, mercapto or deuterium. The C atom marked with a * (star) can be present in an (R) configuration, in an (S)-configuration or a mixture thereof. The invention is characterized in that the abovementioned compounds are free bases with a degree of purity of more than 97 wt %. The invention also relates to a method for the production of highly pure compounds of general formula (I) and to the use thereof in the production of medicaments.

16 Claims, 5 Drawing Sheets

(I)

FOREIGN PATENT DOCUMENTS

| | | | |
|---|---|---|---|
| EP | 1 077 912 B1 | | 7/2002 |
| GB | 624117 | * | 5/1949 |
| GB | 627139 | * | 7/1949 |
| GB | 685696 | | 1/1953 |
| GB | 689835 | | 4/1953 |
| GB | 690274 | | 4/1953 |
| GB | 692931 | | 6/1953 |
| GB | 1025041 | * | 4/1966 |
| GB | 1169944 | * | 11/1969 |
| GB | 1169945 | * | 11/1969 |
| RU | 2199525 | * | 2/2003 |
| WO | 93/23025 | * | 11/1993 |
| WO | 94/11337 | * | 5/1994 |
| WO | WO-94/11337 A | | 5/1994 |
| WO | 96/12477 | * | 5/1996 |
| WO | 98/03067 | * | 1/1998 |
| WO | 98/43942 | * | 10/1998 |
| WO | 98/56359 | * | 12/1998 |
| WO | 99/58478 | * | 11/1999 |
| WO | WO-99/58478 A | | 11/1999 |
| WO | WO 9958478 A1 | * | 11/1999 |
| WO | 00/12069 | * | 3/2000 |
| WO | WO-00/12070 A | | 3/2000 |
| WO | 00/27364 | * | 5/2000 |
| WO | 01/34139 | * | 5/2001 |
| WO | WO-01/35957 A | | 5/2001 |
| WO | 02/11702 | * | 2/2002 |
| WO | 02/089773 | * | 11/2002 |
| WO | 03/002059 | * | 1/2003 |
| WO | 03/007918 | * | 1/2003 |
| WO | 03/020241 | * | 3/2003 |
| WO | 03/021271 | * | 3/2003 |
| WO | 03/026564 | * | 4/2003 |
| WO | 03/035599 | * | 5/2003 |
| WO | 03/039464 | * | 5/2003 |
| WO | 03/063834 | * | 8/2003 |
| WO | 03/099268 | * | 12/2003 |
| WO | 03/103637 | * | 12/2003 |
| WO | 03/106421 | * | 12/2003 |
| WO | 2004/019892 | * | 3/2004 |
| WO | WO-2004/089346 A1 | | 10/2004 |

OTHER PUBLICATIONS

Approval letter for tolterodine tartrate, Mar. 25, 1998.*
Abrams et al., "Tolterodine, a new antimuscarinic agent: as effective but better tolerated than oxybutynin in patients with an overactive bladder," 1998, Br. J. Urol. 81:801-810.*
Abstracts from the 26th Annual Meeting of the International Incontinence Society, Aug. 27-30, 1996, Gillberg et al., abstract 33, Neurology and Urodynamics 15:308-309.*
Anderson et al., "Once daily controlled versus immediate release oxybutynin chloride for urge urinary incontinence," 1999, J. Urol. 161:1809-1812.*
Andersson et al., "Pharmacological treatment of urinary incontinence," in Abrams P., Khoury S., Wein A. (Eds), Incontinence, 2nd International Consultation on Incontinence, Plymouth, Plymbridge Distributors Ltd, UK, Plymouth, 2002, pp. 479-511.*
Andersson, "Antimuscarinics for treatment of overactive bladder," 2004, Lancet Neurol. 3:46-53.
Andersson & Hedlund, "Pharmacological perspective on the physiology of the lower urinay tract," 2002, Urology 60 (Suppl. 5A):13-20.
Andersson & Wein, "Pharmacology of the lower urinary tract: basis for current and future treatments of urinary incontinence," 2004, Pharmacol. Rev. 56:581-631.
Appell et al., "Prospective randomized controlled trial of extended release oxybutynin chloride and tolterodine tartrate in the treatment of overactive bladder: results of the OBJECT study," 2001, Mayo Clinic Proceedings 76:358-363.
Breidenbach et al., "Pharmacodynamic profiling of the novel antimuscarinic drug fesoterodine on rat bladder," 2002, Proceedings of the International Continence Society, 32:449.
Brynne et al., Influence of CYP2D6 polymorphism on the pharmacokinetics and pharmacodynamics of tolterodine, 1998, Clin. Pharmacol. Thera. 63:529-539.
Brynne et al., "Tolterodine does not affect the human in vivo metabolism of the probe drugs caffeine, debrisoquine, and omeprazole," 1999, Br. J. Clin. Pharmacol. 47:145-150.

Brynne et al., "Fluoxetine inhibits the metabolism of tolterodine—pharmacokinetic implications and proposed clinical relevance," 1999, Br. J. Clin. Pharmacol. 48:553-563.
Brynne et al., "Ketoconazole inhibits the metabolism of tolterodine in subjects with deficient CYP2D6 activity," 1999, Br. J. Clin. Pharmacol. 48:564-572.
Cawello et al., "Multiple dose pharmacokinetics of fesoterodine in human subjects," 2002, Nauyn-Schmiedeberg's Arch. Pharmacol. 365 (Suppl. 1):428, 2002.
Chancellor et al., "A comparison of the effects on saliva output of oxybutynin chloride and tolterodine tartrate," 2001, Clinical Therapeutics 23:753-760.
Chapple & Udo, "Delay to maximum effect in overactive bladder patients treated with oxybutynin or tolterodine," 2000, European Urology 37(Suppl. 2):84, abstract 335 from the XVth Congress of the European Association of Urology, Brussels, Belgium, Apr. 12-15, 2000.
Chapple et al., "Fesoterodine a new effective and well-tolerated antimuscarinic for the treatment of urgency-frequency syndrome: results of a Phase II controlled study," 2004, Proceedings of the International Continence Society, 34:142.
Clemett & Jarvis, "Tolterodine: a review of its use in the treatment of overactive bladder," 2001, Drugs & Aging 18:277-304.
Cole, "Fesoterodine, an advanced antimuscarinic for the treatment of overactive bladder: A safety update," 2004, Drugs of the Future 29:715-720.
Committee for Proprietary Medicinal Products, "The assessment of the potential for QT interval prolongation by non-cardiovascular medicinal products," CPMP/986/96, Dec. 17, 1997.
Detrol® package insert, Pharmacia & Upjohn Co., Apr. 2004.
Diokno et al., "Tolterodine (Detrol®) improves incontinence and nocturia in urological based study," Apr. 1999, J. Urol. 161 (4 Suppl):256, abstract 987.
Ekstrom et al., "Effects of tolterodine on bladder function in healthy volunteers," Journal of Urology 153(Suppl.):394A, abstract 662 from the 19th Annual Meeting of the American Urological Association, Las Vegas, Apr. 23-28, 1995.
Gardner & Altman, "Confidence intervals rather than P values: estimation rather than hypothesis testing," 1986, Br. Med. J. 292:746-750.
Gillberg et al., "Tolterodine, a new agent with tissue effect selectivity for urinary bladder," 1994, Neurourology and Urodynamics 13:435-436, abstract 60B from International Continence Society 24th Annual Meeting, Prague, Czech Republic, Aug. 1994.
Gillberg et al., "Comparison of the in vitro and in vivo profiles of tolterodine with those of subtype-selective muscarinic receptor antagonists," 1998, European Journal of Pharmacology 349: 285-292.
Hills et al., "Tolterodine," 1998, Drugs 55:813-820.
Jonas et al., "Efficacy and safety of two doses of tolterodine versus placebo in patients with detrusor overactivity and symptoms of frequency, urge incontinence, and urgency: urodynamic evaluation," 1997, World J. Urol. 15:144-151.
Kang et al., "Cardiac ion channel effects of Tolterodine," 2004, J. Pharmacol. Exper. Thera. 308:935-940.
Kershen & Hsieh, "Preview of new drugs for overactive bladder and incontinence: darifenacin, solifenacin, trospium, and duloxetine," Curr. Urol. Rep. 5:359-367.
Klosa, "Eine Neue Synthesemethode der Darstellung von Diarylalkylaminen," 1966, Journal für Praktische Chemie 4:312-334 (in German) with English translation.
Klosa, "Eine Neue Synthese von Diphenylisopropylaminen," 1966, Journal für Praktische Chemie 4:335-340 (in German, with English translation).
Larsson et al., "Tolterodine in the treatment of overactive bladder: analysis of the pooled phase II safety and efficacy data," 1999, Urology 53: 990-998.
Lipinski, et al., "Experimental and computational approaches to estimate solubility and permeability in drug discovery and development settings" Elsevier Advanced Drug Delivery Reviews vol. 23, pp. 3-25, 1997.
Millard et al., "Clinical efficacy and safety of tolterodine compared to placebo in detrusor overactivity," 1999, J. Urol. 161:1551-1555.

Modiri et al., "Effect of muscarinic antagonists on micturition pressure measured by cystometry in normal, conscious rats," 2002, Urology 59:963-968.
Naerger et al., "Effect of tolterodine on electrically induced contractions of isolated human detrusor muscle from stable and unstable bladders," 1995, Neurourology and Urodynamics 14:524-526, abstract 76 from International Continence Society 25th Annual Meeting, Sydney, Australia, Oct. 1995.
Netzer, et al., "Screening lead compounds for QT interval prolongation" Drug Discovery Today vol. 6, No. 2, pp. 78-84, Jan. 2001.
Nilsson et al., "Comparison of a 10 mg controlled release oxybutynin tablet with a 5 mg oxybutynin tablet in urge incontinence patients," 1997, Neurourol. Urodyn. 16:533-542.
Nilvebrant & Sparf, "Receptor binding profiles of some selective muscarinic antagonists," 1988, European Journal of Pharmacology 151:83-96.
Nilvebrant & Sparf, "Differences between Binding Affinities of some Antimuscarinic Drugs in the parotid Gland and those in the Urinary Bladder and Ileum" Acta Pharmacol. et toxicol. vol. 53, No. 4, pp. 304-313, Oct. 1983.
Nilvebrant et al., "The in vitro pharmacological profile of tolterodine—a new agent for the treatment of urinary urge incontinence," 1994, Neurourology and Urodynamics 13:433-435, abstract 60A from International Continence Society 24th Annual Meeting, Prague, Czech Republic, Aug. 1994.
Nilvebrant et al., "Tolterodine is not subtype (m1-m5) selective but exhibits functional bladder selectivity in vivo," 1996, Neurourology and Urodynamics 15:310-311, abstract 34 from the 26th Annual Meeting of the International Continence Society, Athens, Greece, Aug. 27-30, 1996.
Nilvebrant, "Tolterodine and terodiline—different pharmacological profiles," pp. 141-142, abstract 181a, from the 27th Annual meeting of the International Continence Society, Yokohama, Japan, Sep. 1997.
Nilvebrant et al "Tissue distribution of tolterodine and its metabolites: low penetration into the central nervous system," 2000, European Urology 37(Suppl. 2):84, abstract 333 from the XVth Congress of the European Association of Urology, Brussels, Belgium, Apr. 12-15, 2000.
Nilvebrant, "The mechanism of action of tolterodine," 2000, Reviews in Contemporary Pharmacotherapy 11:13-27.
Olsson et al., "Food increases the bioavailability of tolterodine but not effective exposure," 2001, J. Clin. Pharmacol. 41:298-304.
Olsson & Szamosi, "Food does not influence the pharmacokinetics of a new extended release formulation of tolterodine for once daily treatment of patients with overactive bladder," 2001, Clinical Pharmacokinetics 40:135-143.
Olsson & Szamosi, "Multiple dose pharmacokinetics of a new once daily extended release formulation versus immediate release tolterodine," 2001, Clinical Pharmacokinetics 40:227-235.
Pharmacology/Toxicology Review from Application No. 21-518, Center for Drug Evaluation and Research, pp. 1-3.
Rentzhog et al., "Efficacy and safety of tolterodine in patients with detrusor instability: a dose ranging study," 1998, Br. J. Urol. 81:42-48.
Roy, et al., "HERG, a Primary Human Ventricular Target of the Nonsedating Antihistamine Terfenadine" Circulation vol. 94, No. 4, pp. 817-823, Aug. 15, 1996.
Sachse et al., "Pharmacodynamics of multiple dose treatment with the novel antimuscarinic drug fesoterodine," 2002, Nauyn-Schmiedeberg's Arch. Pharmacol. 365 (Suppl. 1):413.
Sachse et al., "Safety and pharmacokinetics of the novel bladder-selective antimuscarinic drug fesoterodine in populations of different age or gender," 2002, Proceedings of the International Continence Society, 32:441.
Sachse et al., "Safety and pharmacokinetics of the novel bladder-selective antimuscarinic fesoterodine in populations of different ethnic origin," 2003, Proceedings of the International Continence Society, 33:377.
Sachse et al., "Dose-proportional pharmacokinetics of the new antimuscarinic fesoterodine," 2003, Nauyn-Schmiedeberg's Arch. Pharmacol. 367 (Suppl. 1):446.
Sachse et al., "Pharmacodynamics and pharmacokinetics of ascending multiple oral doses of the novel, bladder-selective antimuscarinic fesoterodine," 2003, Eur. Urol. Suppl 2:111.
Sachse et al., "Concomitant food intake does not significantly influence the pharmacokinetics of the novel, bladder-selective antimuscarinic fesoterodine," 2004, Proceedings of the International Continence Society, 34:580.
Sachse et al., "Safety, tolerability and pharmacokinetics of fesoterodine in patients with hepatic impairment," 2004, Proceedings of the International Continence Society, 34:585.
Sachse et al., "Safety, tolerability and pharmacokinetics of fesoterodine after co-treatment with the potent cytochrome P450 3A4 inhibitor ketoconazole," 2004, Proceedings of the International Continence Society, 34:586.
Sachse et al., "Clinical pharmacological aspects of the novel bladder-selective antimuscarinic fesoterodine," 2004, Progrès en Urologie, 14 (Suppl. 3):58.
Stahl et al., "Urodynamic and other effects of tolterodine: a novel antimuscarinic drug for the treatment of detrusor overactivity," 1995, Neurourol. Urodyn. 14:647-55.
Teuvo et al "Extended release tolterodine compared with immediate release tolterodine for the treatment of overactive bladder," 2000, European Urology 37(Suppl. 2):84, abstract 334 from the XVth Congress of the European Association of Urology, Brussels, Belgium, Apr. 12-15, 2000.
Van Kerrebroeck et al., "Tolterodine once daily: superior efficacy and tolerability in the treatment of the overactive bladder," 2001, Urology 57:414-421.
Van Kerrebroeck et al., "Clinical efficacy and safety of tolterodine compared to oxybutynin in patients with overactive bladder," 1997, Neurourol. Urodyn. 16:478-479, abstract No. 91 from the 27th Annual meeting of the International Continence Society, Yokohama, Japan, Sep. 1997.
Versi et al., "Dry mouth with conventional and controlled release oxybutynin in urinary incontinence," 2000, Obstet. Gynecol. 95:718-721.
Wefer et al., "Tolterodine: an overview," 2001, World Journal of Urology 19:312-318.

* cited by examiner

Diagrammatic composition of a monolithic TTS

Patch, surface area = 2.545 cm$^2$

Human skin, surface area = 2.545 cm$^2$, ~ 250 μm

Silicone membrane, surface area = 2.545 cm$^2$, 150 μm

Diffusion cell, surface area = 1.131 cm$^2$
With acceptor, surface area = 0.552 cm$^2$

HIGH PURITY BASES OF 3,3-DIPHENYLPROPYLAMINO MONOESTERS

CROSS-REFERENCE TO RELATED APPLICATIONS

This application is a divisional application of, and claims the benefit of and priority to, U.S. patent application Ser. No. 10/532,836, filed 26 Apr. 2005, which claims the benefit of and priority to International Patent Application No. PCT/EP04/003567, filed 3 Apr. 2004, which claims benefit of and priority to German Patent Application No. 10315917.7, filed 8 Apr. 2003, and which is incorporated herein by reference in its entirety.

This invention concerns high purity bases of 3,3-diphenylpropylamino monoesters, their manufacture and their use as drugs, in particular for transdermal and transmucosal administration.

The proportion of seniors within the total population has gone up significantly in the past 50 years. Bladder dysfunctions belong to the most common geriatric diseases in this group. Therefore, ever greater and more specific significance is being attached to the development of a most effective and gentle treatment of bladder complaints.

In the case of urge incontinence the dysfunction lies in a malfunction of the bladder muscle. Frequently the cause is a stimulation or more precisely a hyperactivity of the muscarinic receptors. For this reason use of the antimuscarinic active ingredients Tolterodin and Oxybutynin is preferred for the treatment of the hyperactive bladder and the associated symptoms such as increased urinary urgency, abnormally frequent micturation or nocturia.

However, oxybutynin is an effective antimuscarinic agent that has serious side effects. Notably the pronounced dryness of the mouth is felt by many patients to be extremely unpleasant.

By comparison with Oxybutynin Tolterodin appears to exhibit lower muscarinic side effect rates. In an organism Tolterodin is predominantly dealkylated into active main metabolites 2-[3-(1,1-diisopropylamino)-1-phenylpropyl]-4-(hydroxy methyl)phenol by the cytochrome P450-isoenzyme 2D6 as well as—slowly—into inactive metabolites by the cytochrome P 450 isoenzyme 3A4.

Since Tolterodin is metabolized exclusively through the P450-isoenzyme, there is the potential danger of interactions with the breakdown of other agents, for example, with Warfarin (Colucci, Annals of Pharmacotherapy 33, 1999, 1173), antimycotics such as Ketoconazol (Brynne, Br J Clin Pharmacol 48, 1999, 564) macrolide antibiotics or protease inhibitors. This danger is present particularly in the case of the so-called slow metabolizers, which have a lack of 2D6, metabolize Tolterodin exclusively through 3A4 and exhibit a distinctly increased Tolterodin concentration in plasma.

WO 99/58 478 describes new derivates of 3,3-diphenylpropylamines as active muscarinic ingredients. The disclosed 3,3-diphenylpropylamine-derivates are prodrugs from 2-[3-(1,1-diisopropylamino)-1-phenylpropyl]-4-(hydroxy-methyl)phenol and are hydrolyzed by esterases upon entering through biological membranes as well as in plasma. For this reason the 2D6 dependent degradation device does not apply.

In contradistinction to Tolterodin such 3,3-diphenylpropylamine derivates, for example, 2-[3-(1,1-Diisopropylamino)-1-phenylpropyl]-4-(hydroxy methyl)phenyl isobutyrate (INN: fesoterodine), therefore do not show a tendency towards accumulation even in the case of slow metabolizers, they do not interfere with P450 inductors/inhibitors and they possess an advantageous safety profile with regard to potential interactions of active ingredients and accumulation of active ingredients.

Therefore, the need arose to make the advantages of the 3,3-diphenylpropylamine derivate described in WO 99/58478, particularly the advantages of the fesoterodine, available to the collective of patients. The metabolism method of Tolterodin and the disadvantages of Oxybutynin (dry mouth) alone make clear the medical need for a medicine that does not exhibit the disadvantages of both of the previously named substances.

The bases of 3,3-diphenylpropylamines published in WO 99/58478 are manufactured by 2-(3-diisopropylamino-1-phenylpropyl)-4-hydroxymethylphenol being converted under alkaline conditions with an appropriate acid chloride, for example, isobutyric acid chloride (see Example Execution 3aa of WO 99/58478).

This reaction, however, only leads disadvantageously to approximately 90% up to a maximum approximate 94% of the desired main product (B). The product consistently contains 6-10% impurities of the starting substance (A), the used acylation agent as well as undesired reaction products in the form of the corresponding di-ester of the acylating reagent used (C) of the monoester (D) of the 4-hydroxy group (see FIG. 1) as well as by dimerization/polymerization.

Attempts by the inventor of this patent application to make the synthesis reaction more selective by, for example, varying the amount of the acylating reagent and/or the acylating conditions (temperature, solvent, concentrations, sequence of the addition, among other things), did not lead to the desired result.

Even extensive trials to purify the high purity base from the product mix in the amounts required for pharmaceutical purposes using conventional procedures remained unsuccessful.

A purification by crystallization is eliminated because the bases of the general Formula I, for example, fesoterodine, are present as viscous oils according to the manufacturing process described in EP 1 077 912 and up to now are not able to be crystallized from the product mix.

Even attempts to purify by distillation did not lead to the desired success.

However, a purity of only 90-96 percent by weight is not adequate for pharmaceutical preparations. Rather a purity of above 97 percent by weight is preferred in general. Therefore a need for high purity free bases of 3,3-diphenylpropylamines existed.

WO 01/35957 teaches stable, crystalline salts of 3-3-diphenylpropylamine derivates, which, compared with the amorphic salts have the advantage of higher stability and higher purity.

Salts of this sort are basically suitable for therapeutic administration and may, for example, be used for oral or parenteral treatment.

For a few applications, for example, the transdermal or transmucosal application, the salt of the active ingredient is less suitable in many situations because its ionized form hinders passage of the skin or the mucous membrane in therapeutically effective amounts. If a transdermal or transmucosal application is desired, then the active ingredient that contains amines has to be frequently applied in the form of the base.

Figure 1:
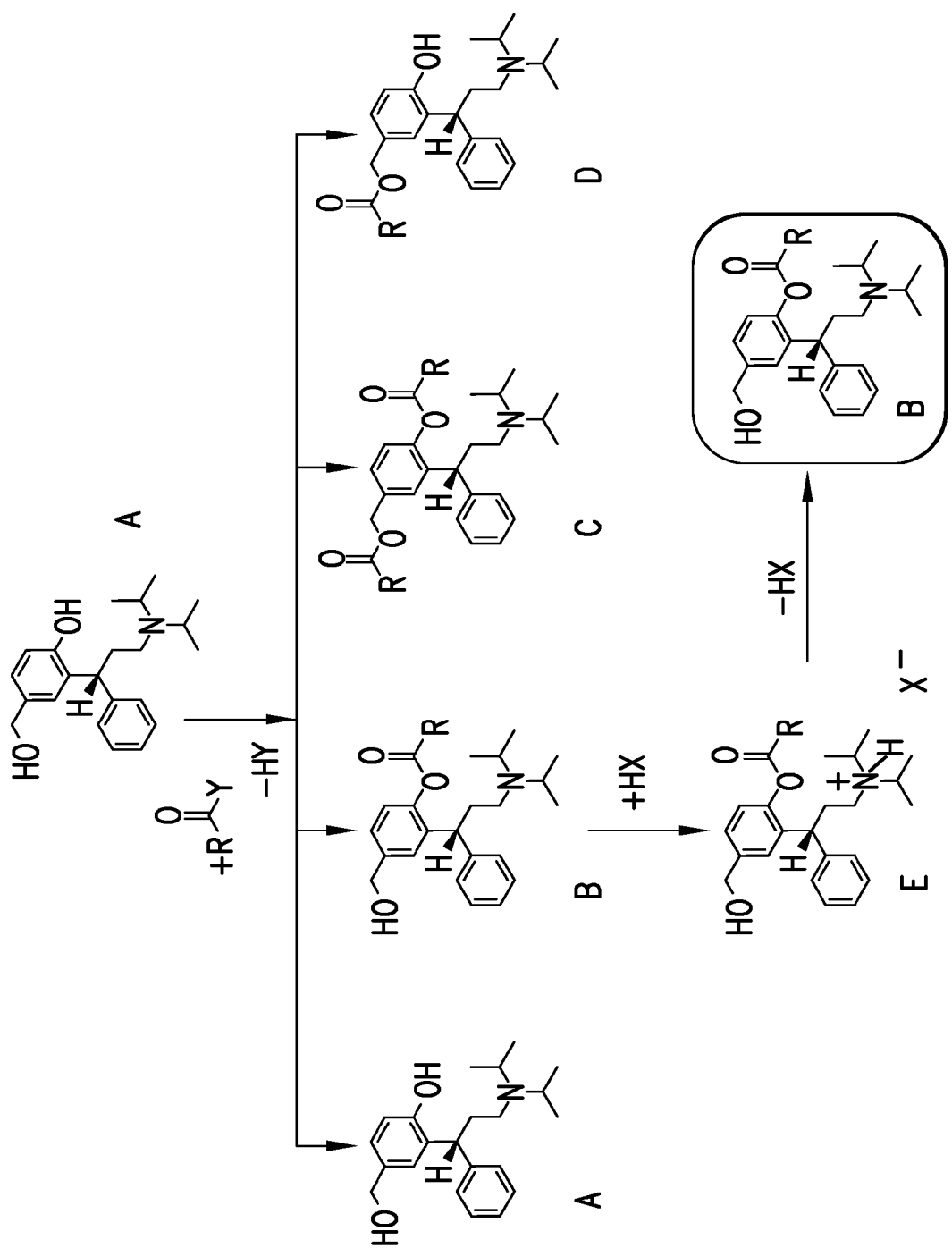
FIG. 1 illustrates a general procedure that can be used for the manufacture of fesoterodine base.

Surprisingly, it was now found that a free base of the general Formula I (see below) could be yielded in a purity of consistently above 97 percent by weight, preferably above 98 percent by weight, especially preferably above 98.5 percent by weight and notably especially preferably above 99 percent by weight and with a high yield above 80% (mol %) if the free base is manufactured by releasing it with an appropriate regency from a high purity, crystalline salt.

One aspect of the invention is therefore the use of a compound of Formula I

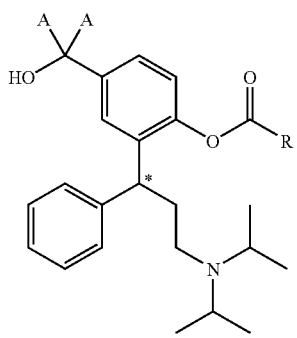

Formula I in which A means hydrogen or deuterium, R stands for a group that is selected from $C_{1-6}$,-alkyl, $C_{3-10}$-cycloalkyl or phenyl, which may each be substituted with $C_{1-3}$-alkoxy, fluorine, chlorine, bromine, iodine, nitro, amino, hydroxyl, oxo, mercapto or deuterium and where the C-atom marked with a star "*" may be present in the (R)-configuration, the (S)-configuration or as a mixture of it,
characterized by the fact that the free base is present in a degree of purity of above 97 percent by weight, preferably above 98 percent by weight, especially preferably above 98.5 percent by weight and notably, especially preferably above 99 percent by weight.

In a preferred form of execution R is selected from the group methyl, ethyl, isopropyl, 1-propyl, 1-butyl, 2-butyl, tertiary-butyl, iso-butyl, pentyl, hexyl $C_4$-$C_8$ cycloalkyl or phenyl.

In an especially preferred form of execution R is isopropyl (i-Pr) so that the compound is 2-[3-(1,1-diisopropylamino)-1-phenylpropyl]-4-(hydroxy methyl)phenyl isobutyrate (fesoterodine base).

In one form of execution of the invention the compounds of the general Formula 1 are present as a racemate, meaning as mixtures of the (R)- and (S) configured molecules.

In another preferred form of execution the C-atom marked with a star "*" is present in (R)-format, whereby preferably over 98 percent by weight of the compound, especially preferably over 99 percent by weight of the compound and notably especially preferably over 99.5 percent by weight of the compound is present in the (R)-configuration.

In a notably especially preferred form of execution the compound is the high purity free base from (R)-2-[3-(1,1-diisopropylamino)-1-phenylpropyl]-4-(hydroxy methyl) phenyl isobutyrate (fesoterodine base) with a purity content of over 97 percent by weight, preferably above 98 percent by weight, especially preferably above 98.5 percent by weight and notably especially preferably above 99 percent by weight.

In this application "$C_{1-6}$ alkyl" is understood to be a straight chain or branched chain hydrocarbon group with 1-6 C-atoms. Preferred $C_{1-6}$ alkyls are non-substituted straight or branch chain groups, in particular selected from the group of methyl, ethyl, propyl, isopropyl, 1-butyl, 2-butyl, tertiary-butyl, pentyl and hexyl.

The expression "$C_{3-10}$ cycloalkyl" is understood to mean a cyclical hydrocarbon group with 3-10 hydrocarbon atoms.

In this application "high purity" is understood to mean a degree of purity of the monoester of the general Formula I of above 97 percent by weight minimum, preferably above 98 percent by weight, especially preferably above 98.5 percent by weight and notably especially preferably above 99 percent by weight, meaning that an appropriately low proportion of diesters, dihydroxy compounds, 4-monoesters or polymers is present. The degree of purity is determined as described in the techniques section.

In the sense of the invention the expression "free base" is understood to mean that less than 10 percent by weight, preferably less than 5% or 3%, especially preferably less than 1% is of the compound of the general Formula I is present in the salt form. The salt content is thereby determined as described in the techniques section.

The high purity bases of the general Formula I in compliance with the invention can be manufactured by their release from the high purity, crystalline salts of the general formula II:

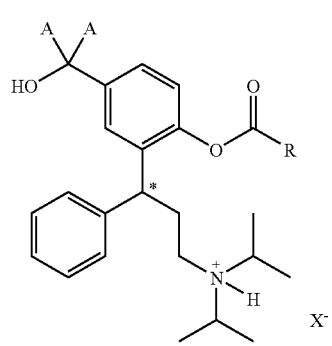

Formula II where A and R have the significance given above, X⁻ is the acid residue of a physiological compatible acid and where the C-atom marked with "*" (a star) can be present in the (R)-configuration, in the (S)-configuration or as a mixture thereof.

In the course of this the anion of one of the subsequently named acids comes into consideration as an acid residue X⁻:

Hydrochloric acid, hydrobromic acid, phosphoric acid, sulphuric acid, nitric acid, acetic acid, propionic acid, palmitic acid, stearic acid, maleic acid, fumaric acid, oxalic acid, succinic acid, DL-malic acid, L-(−)-malic acid, D-(+)-malic acid, DL-tartaric acid, L-(+)-tartaric acid, D-(−)-tartaric acid, citric acid, L-aspartic acid, L-(+)-ascorbic acid, D-(+)-glucuronic acid, 2-oxopropionic acid (pyruvic acid), furan-2-carboxylic acid (pyromucic acid), benzoic acid, 4-hydroxybenzoic acid, salicylic acid, vanillic acid, 4-hydroxycinnamic acid, gallic acid, hippuric acid (N-benzoyl-glycin), aceturic acid (N-acetyl glycine), phloretin acid (3-(4-Hydroxyphenyl)-propionic acid), phthalic acid, methane-sulphonic acid or orotic acid, where the acid anions hydrogen fumarate and hydrochloride are especially preferred.

The corresponding high purity bases are released from this high purity compound of the general Formula II through the addition of the appropriate base reagents ("release reagents").

The release reagents are, for example, alkaline compounds from the group of
- hydroxides, carbonates and alkaline-, alkaline earth- or ammonium hydrogen carbonates,
- amines, polyamines and alkaline polyamino acids, that may also be present both in a solution and fixed onto carriers,
- alkaline ionic exchangers, where weak alkaline compounds with a $pK_B$ of 8-11 are preferred.

Such reagents are preferred as release reagents that inhibit a precipitation of the bases of the 3,3-diphenylpropylamine monoesters in the particular solvent. In addition, a hydrolysis of the ester bond should be avoided.

For example, in an aqueous environment the conversion of a compound of the Formula II with a hydrogen carbonate leads initially to a water soluble hydrogen carbonate salt of a 3,3-diphenylpropylamine monoester being formed as an intermediate product. When extraction by shaking using an organic solvent, for example, dichloromethane is conducted, the $CO_2$ escapes, and the poor, water soluble free base of the 3,3-diphenylpropyl amino monoester can be gained from the organic phase without further purification as high purity oil.

Precipitation of the base of the 3,3-diphenyl monoester immediately following release, which may result in a lower purity and/or a lower yield, is impeded by this method of execution. Hydrolysis of the ester bond is also avoided.

The hydrogen carbonate salts of the compounds of the general Formula I, especially fesoterodine hydrogen carbonate, are explicitly made the object of the invention as preferred intermediate products.

An alkaline-, earth alkaline or ammonium hydrogen carbonate is especially preferred as the releasing reagent, whereby sodium hydrogen carbonate is notably especially preferred.

Therefore, in a preferred manufacturing process the salt of the Formula II is first absorbed in water and laced with a base releasing agent, for example, a hydrogen carbonate. This is then extracted by shaking using an appropriate solvent and the organic phase evaporated to a low small bulk until the high purity base of the Formula I remains behind as a viscous oil. Such a process is shown in more detail in Example Execution 1C.

Solvents that are suitable for purification of the free base are in particular dichloromethane, tertiary-butyl-methyl ether, diethyl ether, ethyl methyl ketone as well as toluene, where dichloromethane is especially preferred.

In an alternative manufacturing process the high purity salt of the Formula II is absorbed in an appropriate solvent and then conducted over a carrier, which contains immobilized ionic exchangers, for example. The eluate then contains the high purity base of the general Formula I.

(R)-2-[3-(1,1-diisopropylamino)-1-phenylpropyl]-4-(hydroxy methyl)phenyl isobutyrate hydrogen fumarate is especially preferred for use as the initial compound of the Formula II for the production of the high purity free base of (R)-2-[3-(1,1-diisopropylamino)-1-phenylpropyl]-4-(hydroxy methyl)phenyl isobutyrate.

One object of the invention is therefore a procedure for the manufacture of a high purity free base of the general Formula I

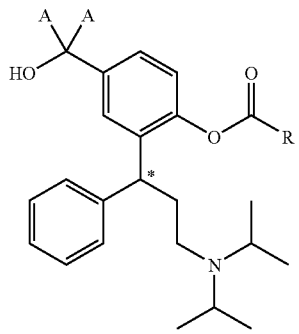

Formula I in which A means hydrogen or deuterium, R stands for a group that is selected from $C_{1-6}$-alkyl, $C_{3-10}$-cycloalkyl or phenyl, which may each be substituted with $C_{1-3}$-alkoxy, fluorine, chlorine, bromine, iodine, nitro, amino, hydroxyl, oxo, mercapto or deuterium and where the C-atom marked with a star "*" may be present in the (R)-configuration, the (S)-configuration or as a mixture of it in a purity of above 97 percent by weight minimum, preferably above 98 percent by weight, especially preferably above 98.5 percent by weight and notably especially preferably above 99 percent by weight, whereby the procedure is characterized through the release of the high purity free base of the general Formula I from a crystalline salt of the general Formula II

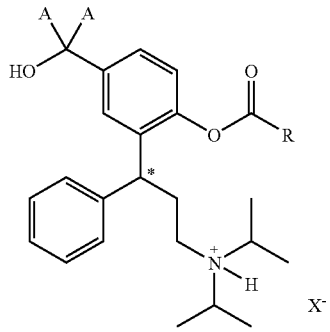

Formula II with a purity of 97 percent by weight, preferably above 98 percent by weight, especially preferably above 98.5 percent by weight and notably especially preferably above 99 percent by weight, whereby A and R have the significance given above, $X^-$ is the acid residue of a physiological compatible acid and where the C-atom marked with "*" (a star) can be present in the (R)-configuration, in the (S)-configuration or as a mixture thereof.

The inventive manufacturing process is preferably used to manufacture high purity bases of the general Formula I, in which the C-atom identified with "*" is present in the (R)-configuration and/or in which the substituent R is selected from the methyl, ethyl, isopropyl, 1-propyl, 1-butyl, 2-butyl, tertiary-butyl, iso-butyl, pentyl and hexyl group.

The inventive manufacturing process preferably serves for the manufacture of the high purity free base (R)-2-[3-(1,1-diisopropylamino)-1-phenylpropyl]-4-(hydroxy methyl) phenyl isobutyrate, whereby (R)-2-[3-(1,1-diisopropylamino)-1-phenylpropyl]-4-hydroxy methyl)phenyl isobutyrate hydrogen fumarate is especially preferred for use as the initial compound of the Formula II.

The production of the high purity salts of the Formula II is known from WO 01/35957. For this purpose a solution of 2-[3-(1,1-diisopropylamino)-1-phenylpropyl]-4-(hydroxy methyl)phenol is converted in a base solution with an acid chloride, for example, isobutyric acid chloride. The resulting base with a low purity content is then laced with an acid, for example, fumaric acid, while being heated. The resulting salt of the general Formula II can then be crystallized out in appropriate solvents. The crystals are then dissolved again and re-crystallized.

This process can be repeated if necessary until a compound of the Formula II is obtained with the desired degree of purity. The high purity free base of the Formula I is yielded from these salts as described above.

As a general rule the yield of high purity free base of the Formula I in amounts to above 90% of the theory based on the amount of the 3,3-diphenylaminomonoester of the Formula II used.

Table 1 shows the clean-up of the fesoterodine base using the inventive process

| Process Step[a] | Purity B or E (%) |
|---|---|
| 1. Chemical synthesis of B from A | 94.37 |
| 2. Production of the salt E from B (1) | 92.58 |
| 3. Re-crystallization of the salt E from (2.) | 99.32 |
| 4. Released high purity base B from E (3.) | 99.14 |

[a] A, B, C, E: R = i-Pr, see FIG. 1/4

The inventive pure bases of the general Formula II are present in the form of an oil following manufacture and are stable at −20° C.

At higher temperatures, for example at 2° C.-8° C. the inventive free bases are preferably stored in the presence of drying agents.

The inventive procedure allows for the first time the efficient isolation of the free base of the general Formula I in a high purity form. The procedure is up-scalable and makes manufacture of the high purity compounds possible on an industrial scale and for the first time makes the high purity bases of the general Formula I containing pharmaceutical formulations available.

A further aspect of this invention is therefore a pharmaceutical formulation that comprises a compound of the general Formula I, which comprises

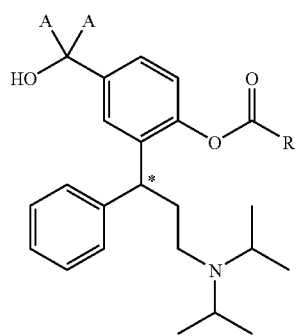

Formula I as well as at least one pharmaceutically acceptable carrier, whereby A is either hydrogen or deuterium, R stands for a group that is selected from $C_{1-6}$-alkyl, $C_{3-6}$-cycloalkyl or phenyl, which may each be substituted with $C_{1-3}$-alkoxy, fluorine, chlorine, bromine, iodine, nitro, amino, hydroxyl, oxo, mercapto or deuterium and where the C-atom marked with a star "*" may be present in the (R)-configuration, the (S)-configuration or as a mixture of it in a purity of above 97 percent by weight minimum, preferably above 98 percent by weight, especially preferably above 98.5 percent by weight and notably especially preferably above 99 percent by weight.

In a further preferred form of execution of the invention the inventive pharmaceutical formulation contains a compound of the general Formula I where R is selected out of the methyl, ethyl, 1-propyl, isopropyl (i-Pr), 1-butyl, 2-butyl, tertiary-butyl, iso-butyl, pentyl and hexyl group, whereby it is especially preferable that R be an isopropyl, and whereby it is especially preferable the C-atom identified with "*" is present in the (R)-configuration.

In a notably especially preferred form of execution of the invention the pharmaceutical formulation of the free base from (R)-2-[3-(1,1-diisopropylamino)-1-phenylpropyl]-4-(hydroxy methyl)phenyl isobutyrate (fesoterodine free base) with a degree of purity of 97 percent by weigh minimum, preferably above 98 percent by weight, especially preferably above 98.5 percent by weight and notably especially preferably above 99 percent by weight.

Since the inventive free bases are sensitive to hydrolysis or more precisely to interchange esterification, the storage of the pharmaceutical formulations should preferably be done at <25° C., especially preferably at <8° C. and in the presence of drying agents.

Preferably the inventive free bases are present in the pharmaceutical formulation in a slightly acidic environment, meaning at a pH of 3-7, preferably pH 3-6 or pH 3-5, since the stability of the free bases is highest under these conditions.

Furthermore, for reasons of stability it is preferred that the pharmaceutical formulations be free from short chain $C_{1-8}$ alcohols and from $C_{1-4}$ alcohols in particular.

The arrangement of the pharmaceutical formulation primarily depends on the mode of administration as well as on the desired properties of the respective form of administration.

Consequently, for example the possibilities are:
Oral forms: Powders, granulates, tablets, dragees, capsules, solutions or suspensions
Parenteral forms: solutions or suspensions
Transdermal forms: transdermal therapeutic systems (TTS), ointments, creams, foils, lotions, sprays, gels or foams.
Transmucosal forms:
   buccal or sublingual forms: quick releasing tablets, sprays, drops, wafer-shaped forms of drugs as well as mucoadhesive pellets or patches
   nasal forms: Lotions, drops, sprays, ointments
   pulmonal forms: aerosols
Essentially, the auxiliary agents known to the specialist in the area of pharmaceutical technology are qualified as pharmaceutically acceptable carriers, such as they are described in Sucker, Fuchs and Speiser, Pharmazeutische Technologie, Georg Thieme Verlag, Stuttgart, for example, and other reviews on appropriate forms of drugs.

Such a pharmaceutical formulation may be conventional but may also be arranged as a fast-releasing or retarding formulation dependent upon the special requirements of the patient.

The bases of the general Formula I, for example, fesoterodine, have emerged as passing surprisingly well through membranes. For this reason suitable pharmaceutical formulations for transdermal or transmucosal applications in particular are being offered.

It is preferred that the inventive high purity bases of the general Formula I with controlled release of the active ingredient be used in pharmaceutical formulations for the transdermal or transmucosal application. The pharmaceutical formulations, which after an initial burst effect phase, are ensuring a constant flux rate through the skin or mucous membrane of a patient over a minimum of 24 hours, preferably over a minimum of 48 hours, are especially preferred.

To guarantee such controlled delivery of an active ingredient the pharmaceutical formulation contains at least one polymer layer in which a high purity base of the general Formula I is dispersed or dissolved.

The release behavior of the active ingredient can be influenced through the composition of such a polymer layer. So, for example, the solubility behavior of active ingredients in the polymer matrix decisively determines the release of the active agent from transdermal/transmucosal therapeutic systems and by doing so determines the flux rates through the skin or the mucous membrane as well.

Furthermore, the polymer layer may contain pressure sensitive adhesive substances that make the attachment of the pharmaceutical composition to the skin or the mucous membrane of the patient possible.

For example, a buccal formulation may be arranged as a mucoadhesive system from out of which there is retarded release of the active ingredient. Adhesive polymers/copolymers such as PVP, pectin, carbopol, polyacrylates cellulose derivates, chitosane or polyoxyethylene are used for the adhesion to the mucous membrane. Appropriate examples and overviews are found, for example in U.S. Pat. No. 6,210,699; U.S. Pat. No. 4,855,142; U.S. Pat. No. 4,680,323; U.S. Pat. No. 5,700,478; U.S. Pat. No. 4,948,580; U.S. Pat. No. 4,715,369; U.S. Pat. No. 4,876,092; U.S. Pat. No. 5,750,136; Woodley, Clin Pharmacokinet 40, 2001, 77 or Singla, Drug Dev Ind Pharm 26 (2000) 913. These adhesive polymers/copolymers may function as the adhesive outer coating of tablets, for example, but in a buccal patch may also be a component of an adhesive polymer matrix in which the active ingredient is present either dissolved or dispersed (Wong, Int J. Pharm. 178, 1999, 11).

In one form of execution of the invention the pharmaceutical formulation for the transdermal delivery of a high purity base of the Formula I is therefore arranged as a buccal formulation, in particular as a buccal patch, which incorporates at a minimum a polymer layer, in which the high purity base of the general Formula I is present either dissolved or dispersed. This polymer layer that contains the high purity base preferably has mucoadhesive properties.

In a particularly preferred form of execution of the invention the pharmaceutical formulation for the transdermal delivery of a high purity base of the Formula I is arranged as a transdermal patch.

Transdermal patches (also often identified as transdermal therapeutic systems TTS) may be categorized in different ways whereby a distinction is often made between the following three main groups:

The reservoir type, in which the active ingredient is present in a solution or a gel and which are applied to the skin of the patient using a speed-regulating membrane.

The matrix type, which can be further subdivided into

The laminate type, in which the active ingredient is present in a layer (matrix) of non-adhesive polymers. The TTS may contain other layers for attachment to the skin, for example, an adhesive layer; however it may also be attached to the skin by separate adhesive foils (over tapes).

Figure 4:
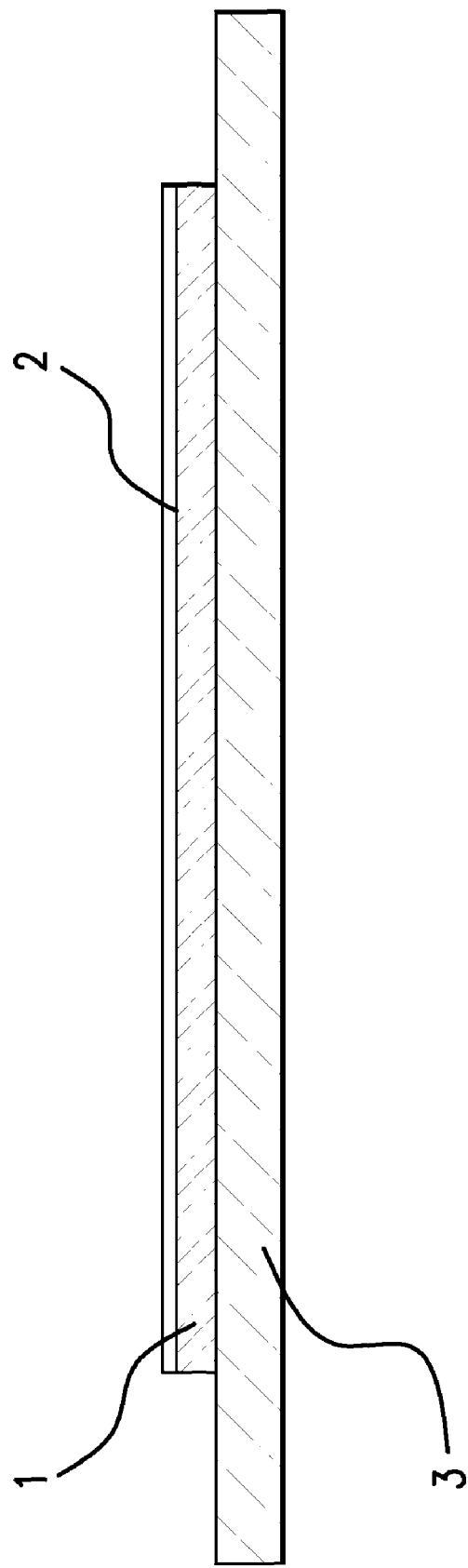
FIG. 4 illustrates the typical structure of a monolithic TTS.
Figure 5:
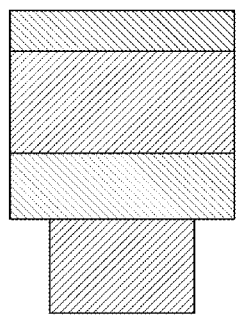
FIG. 5 illustrates a TTS with a surface of 2.545 cm² applied on a surface similar to human skin, where the skin lay on a silicone membrane acceptor side up.

The monolithic type, in which the active ingredient is present in a contact adhesive layer (adhesive matrix). An example for a typical structure of a monolithic TTS is reproduced in FIG. 4/4. The model monolithic TTS consists of the adhesive matrix which contains the active ingredient (1), a backing being impermeable and inert for the ingredients of the adhesive matrix, which after the administration of the patch on the skin of the patient finds itself on the site of the TTS remote to the skin (2) as well as a detachable layer for protection which is removed immediately before application of the TTS onto the skin (3).

Iontophoretic systems in which the flux of the active ingredient through the skin is supported by the application of an electrical current.

Especially preferred drugs in the sense of this invention are TTS of the matrix type, whereby monolithic TTS, in which the active ingredient is present in the adhesive matrix, are notably especially preferred.

Under the term "polymer matrix" or "matrix" in this patent application a layer or paste that contains polymers is comprehended whereby the term "polymer matrix" is incorporated by this.

In this patent application the expression "total weight of the polymer matrix" is understood to mean the weight of the polymer matrix including the active ingredient introduced into it and possible auxiliary agents.

Non-limiting examples for adhesive polymers/copolymers that are suitable for the manufacture of transdermal devices and which may contain the active ingredient of the general Formula I in dissolved, partially dissolved or dispersed form are silicone adhesives, ethyl vinyl acetate (EVA)-adhesives, styrene block copolymer (SXS)-adhesives, acrylate adhesives, polyurethane adhesives, vinyl acetate adhesives as well as the adhesive gums, for example, polyisobutylene, polybutadiene, neoprene or polyisoprene as well as suitable mixtures of these adhesives.

The polymer adhesives known in patch technology of the silicone type, of the acrylate type, the SxS type, the ethyl vinyl acetate (EVA type) that are known from the state of the art are particularly suitable as contact adhesives. The properties of these contact adhesives will be further explained more closely below.

The dosing of the compounds in compliance with invention is dependent on the age, weight a status of the patient, the type of application and the interval. Generally speaking the effective daily dose lies in the 0.5-20 mg range. Typically, in the case of oral administration at least 3 mg/day, for example 3-15 mg/day, preferably 4-12 mg/day is used. A typical transdermal or transmucosal daily dose, for example, for fesoterodine, for an adult patient lies, for example, at a minimum of 3 mg, preferably in the 3-15 mg range and especially preferred between 4 and 12 mg.

A pharmaceutical composition, which is suitable for once daily administration should therefore preferably contain 3-15 mg of a high purity base of the general Formula I.

For safety reasons, if the pharmaceutical composition is a transdermal formulation, it will generally be given around twice the amount of active ingredient to be administered. A typical formulation for transdermal delivery of a high purity compound of the general Formula I in compliance with the invention consequently contains at least 6 mg active ingredient, but depending on the level of dosage and the application interval, it may also contain more than 10 mg, 20 mg, 30 mg, 40 mg or 50 mg of the high purity active ingredient of the general Formula I, for example, fesoterodine, per dosing unit. If a five or even seven day application interval is scheduled the active ingredient content of an individual dosing unit may also be above 70, 80, 90 or even over 100 mg.

In this patent application the expression "dosing unit" is understood to mean a pharmaceutical formulation that contains a defined amount of active ingredient and that releases this following the one-time administration in patents over a predetermined period of time in a therapeutically effective amount. In this patent application the term "dosing unit" comprises both a tablet for application three times a day as well as a patch for weekly administration.

An object of this invention is therefore a dosing unit that comprises at least 3 mg of a compound of the general Formula I,

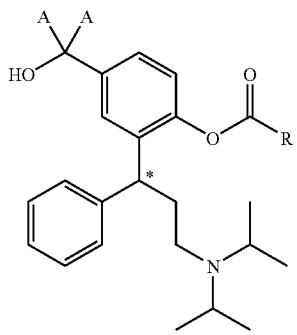

Formula I as well as at least one pharmaceutically acceptable carrier, whereby A is either hydrogen or deuterium, R stands for a group that is selected from $C_{1-6}$-alkyl, $C_{3-6}$-cycloalkyl or phenyl, which may each be substituted with $C_{1-3}$-alkoxy, fluorine, chlorine, bromine, iodine, nitro, amino, hydroxyl, oxo, mercapto or deuterium and where the C-atom marked with a star "*" may be present in the (R)-configuration, the (S)-configuration or as a mixture of it and whereby the free base of the compound I is present in a purity of above 97 percent by weight minimum, preferably above 98 percent by weight, especially preferably above 98.5 percent by weight and notably especially preferably above 99 percent by weight.

In other forms of execution of the invention the dosing unit is given at least 10 mg, 20 mg, 30 mg, 40 mg, 50 mg, 70 mg, 80 mg, 90 mg or even over 100 mg high purity active ingredient of the general Formula I.

In a preferred form of execution of the invention the inventive dosing unit contains a compound of the general Formula I where R is selected out of the methyl, ethyl, 1-propyl, isopropyl (i-Pr), 1-butyl, 2-butyl, tertiary-butyl, iso-butyl, pentyl and hexyl group, whereby it is especially preferred that R is an isopropyl and whereby it is especially preferable that the C-atom identified with "*" be present in the (R)-configuration.

In a notably especially preferred form of execution of the invention the dosing unit contains the free base from (R)-2-[3-(1,1-diisopropylamino)-1-phenylpropyl]-4-(hydroxy methyl)phenyl isobutyrate (fesoterodine free base) with a degree of purity of 97 percent by weight minimum, preferably above 98 percent by weight, especially preferably above 98.5 percent by weight and notably especially preferably above 99 percent by weight.

If the pharmaceutical formulation is arranged as a transdermal form of administration, the flux rate through the skin of the patient should be as constant as possible in order to avoid fluctuations of the concentration in the plasma.

The daily dose should therefore be administered in the case of an application area of 50 cm², preferably a maximum of 40 cm², in a steady state flux through the human skin of more than 6 μg/cm²/hour, preferably of more than 8 μg/cm²/hour, especially preferably of more than 10 μg/cm²/hour and notably especially preferably of more than 12 μg/cm²/hour, whereby the flux rates are determined according to Tanojo in a model of human skin in-vitro as described in Example Execution 3.2.

The invention also concerns the manufacture of drugs.

The high purity bases in compliance with the invention are for use during manufacture of a medicine, particularly for the treatment of incontinence, notably especially for the treatment of urge incontinence, as well as for the treatment of hyperactivity of the detrusor, pollakisuria, nocturia or imperative urinary urgency.

One aspect of the invention is therefore the use of a free base of the general Formula I,

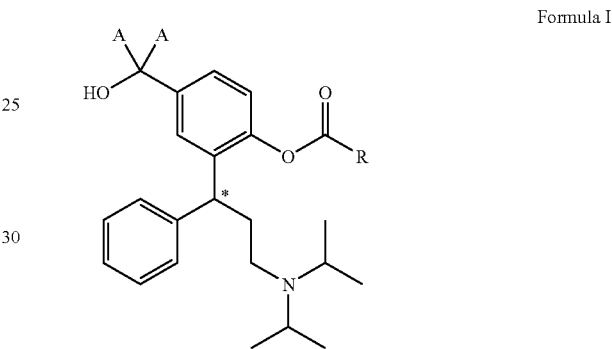

Formula I in which A means hydrogen or deuterium, R stands for a group that is selected from $C_{1-6}$-alkyl, $C_{3-10}$-cycloalkyl or phenyl, which may each be substituted with $C_{1-3}$-alkoxy, fluorine, chlorine, bromine, iodine, nitro, amino, hydroxyl, oxo, mercapto or deuterium and where the C-atom marked with a star "*" may be present in the (R)-configuration, the (S)-configuration or as a mixture of it and whereby the free base is present in a purity of above 97 percent by weight minimum, preferably above 98 percent by weight, especially preferably above 98.5 percent by weight and notably especially preferably above 99 percent by weight for the manufacture of a medicine, preferably a medicine for transdermal or transmucosal delivery.

In a preferred form of execution of the invention the compound of the general Formula I, where R is selected out of the methyl, ethyl, 1-propyl, isopropyl (i-Pr), 1-butyl, 2-butyl, tertiary-butyl, iso-butyl, pentyl and hexyl group, whereby it is especially preferred that R is an isopropyl and whereby it is especially preferred that the C-atom identified with "*" be present in the (R)-configuration, is used for the manufacture of the above names drugs.

The high purity bases of the Formula I may, for example, be used for manufacture of the more available buccal drugs, e.g. sprays, mucoadhesive pellets or fast dissolving wafers, as described in WO 02/02085 for example.

Other preferred medicine forms of the bases of the Formula I are transdermal formulations, for example, ointments, creams, lotions, sprays, pastes, foils or patches containing an active ingredient.

In the course of this the high purity base of the general Formula I is preferably used for the manufacture of a medicine for retarded transdermal or transmucosal delivery and for this purpose is preferably introduced into an adhesive or a non-adhesive polymer matrix.

One object of the invention is therefore the use of a free base of the general Formula I,

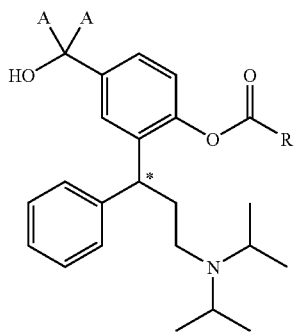

Formula I in which A is hydrogen or deuterium, R stands for a group that is selected from $C_{1-6}$-alkyl, $C_{3-10}$-cycloalkyl or phenyl, which may each be substituted with $C_{1-3}$-alkoxy, fluorine, chlorine, bromine, iodine, nitro, amino, hydroxyl, oxo, mercapto or deuterium and where the C-atom marked with a star "*" may be present in the (R)-configuration, the (S)-configuration or as a mixture of it and whereby the free base is present in a purity of above 97 percent by weight minimum, preferably above 98 percent by weight, especially preferably above 98.5 percent by weight and notably especially preferably above 99 percent by weight,
for the manufacture of a medicine, preferably a medicine for transdermal or transmucosal delivery characterized by the fact that the compound of the Formula I is present either dissolved or dispersed in a polymer layer, preferably in a self-adhesive polymer layer.

In a preferred form of execution of the invention the compound of the general Formula I is used for the manufacture of the above named transdermal medicine, whereby R is selected out of the methyl, ethyl, 1-propyl, isopropyl (i-Pr), 1-butyl, 2-butyl, tertiary-butyl, iso-butyl, pentyl and hexyl group, whereby it is especially preferred that R be an isopropyl and whereby it is especially preferred the C-atom identified with "*" be present in the (R)-configuration.

It is preferable that the high purity compound of the general Formula Ibe present in the form of the free base with a combined salt part of less than 10 percent by weight, especially preferable less than 5% or 3%, notably especially preferable less than 1%.

If the high purity salts from 3,3-diphenylpropylamine derivates known from WO 01/35957, for example, the fumarate salt from fesoterodine, only lead in the case of transdermal delivery to flux rates not sufficient for transdermal treatment, even the addition of loaded molecules such as silicates or Chitosan, for example, or of skin penetration amplifiers like oleic acid or PGML (polyglycol monolaurate) to the matrices containing the active ingredient salt does not lead to satisfactory flux rates (Table 2).

Even an in-situ release of the base from the corresponding salt through the addition of calcium silicate during manufacture of the adhesive matrix, as described in WO 94/07486, does not lead to the flux rates through the human skin desired (Table 2), because the in-situ conversion to the free base is generally not absolute so that too high a proportion of the active ingredient in its protonated form is present in the matrix.

The compound of the general Formula I should therefore be added to the polymer matrix paste, preferably already in the form of the high purity free base at the time of the manufacture of the inventive devices.

TABLE 2

| Lot-No | Contact adhesive | Procedure | Loading of the active ingredient (Percent by weight fesoterodine) | Matrix weight (g/m²) | Flux μg/cm²/Day (in steady state; after 24 hours) | |
|---|---|---|---|---|---|---|
| | | | | | Mouse Skin | Human skin |
| 20111080[1] | Acrylate | Solvent | 15 | 100 | 705 | n.d. |
| 20302060[1] | Acrylate | Solvent | 15 | 87 | n.d. | 332.64 |
| 20111085[1] | EVA | Hot melt | 15 | 84 | 510 | 323.7 |
| 20111086[1] | Silicone | Hotmelt | 15 | 63 | 495 | n.d. |
| 20302062[1] | Silicone | Hotmelt | 15 | 100 | n.d. | 544.89 |
| 20111087[1] | SxS | Hotmelt | 15 | 89 | 460 | 383.8 |
| 20302063[1] | Silicone + PVAc[6] | Hotmelt | 15 | 83 | n.d. | 501.09 |
| 20002031[2] | Acrylate | Solvent | 15 Fumarate | 105 | 27 | n.d. |
| 20104035[2,3] | Acrylate/OL | Solvent | 15 Fumarate | 110 | 84 | n.d. |
| 20106061[4] | Silicone | Solvent | 15 Fumarate | 60 | n.d. | 24.2 |
| 20106043[5] | Silicone | Hotmelt | 15 DiOH[5] | 101 | n.d. | 2.3 | n.d. = not determined;
[1] = fesoterodine was added to the matrix as the free base;
[2] = Comparison example manufactured through the use of fesoterodine-fumarate salt;
[3] = Comparison example manufactured through the use of fesoterodine-fumarate salt with oleic acid as the permeation enhancer;
[4] = Comparison example manufactured through the in-situ release of the base from the fumarate salt into the adhesive matrix;
[5] = Comparison example manufactured through the use of the dihydroxymetabolites (2-[3-(1,1-diisopropylamino)-1-phenylpropyl]-4-(hydroxy methyl)phenol) from fesoterodine;
[6] PVAc = Poly Vinyl Acetate.

Figure 2:
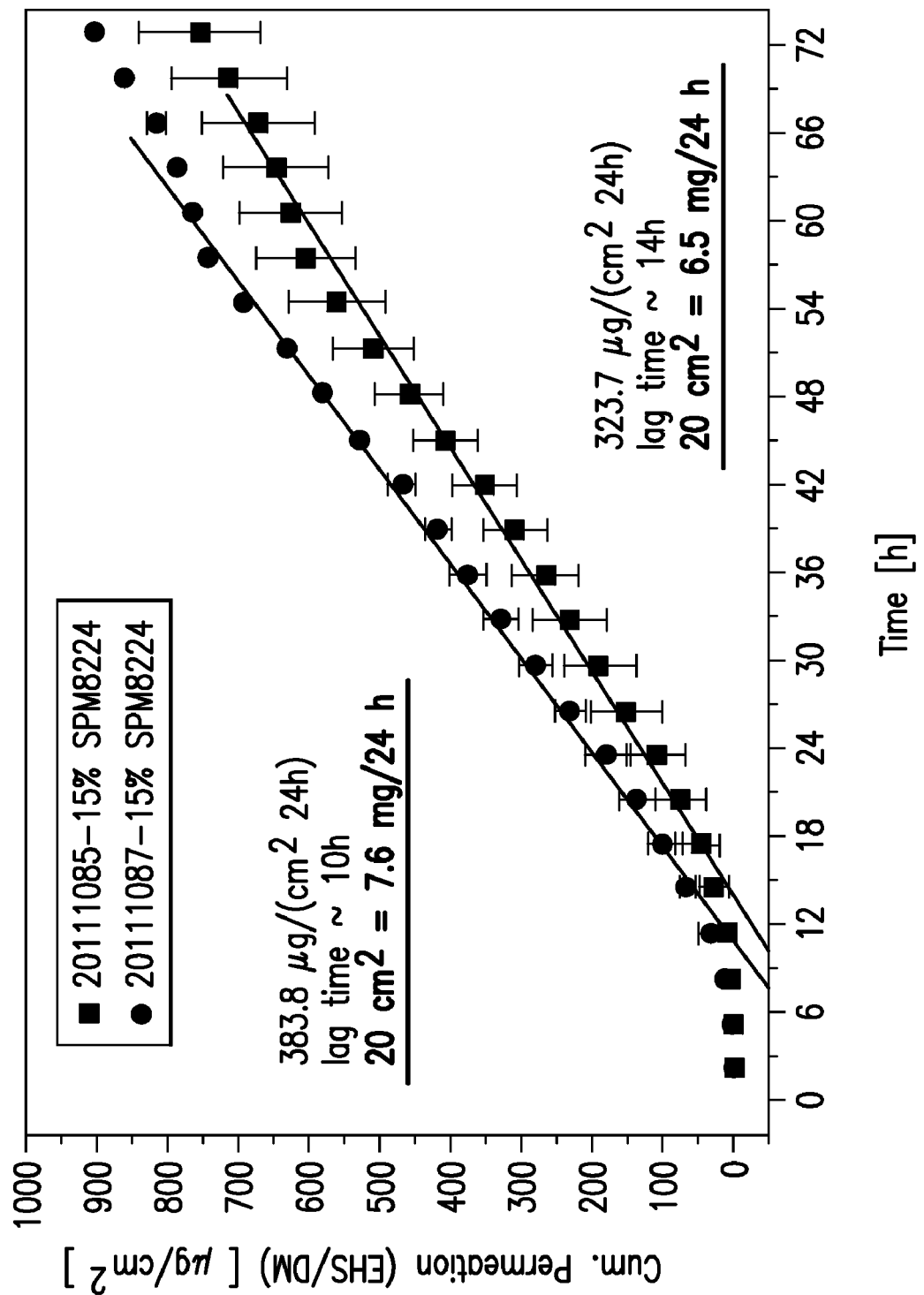
FIG. 2 illustrates the in-vitro flux rate through human skin for the high purity free base of fesoterodine.

FIG. 2 shows that in those cases which the high purity base of (R)-fesoterodine in an amount of 15 percent by weight was introduced into appropriate adhesive matrices of the SXS or EVA type, TTS leads to flux rates that make therapeutically desired daily doses with the corresponding application surface of 5-50 cm² possible in the case of the trials using in-vitro human skin as follows (Table-3):

TABLE 3

Flux rate fesoteradine through human skin (mg/day) based on the TTS size

| Contact adhesive | 5 cm² | 10 cm² | 20 cm² | 30 cm² | 40 cm² | 50 cm² |
|---|---|---|---|---|---|---|
| EVA | 1.6 | 3.2 | 6.5 | 9.7 | 13 | 16 |
| SXS | 1.9 | 3.8 | 7.6 | 11.4 | 15.2 | 19 |
| Silicone/Cer + PVAc | 2.5 | 5 | 10 | 15 | 20 | 25 |
| Acrylate (Durotak 87-4287) | 1.7 | 3.3 | 6.6 | 10 | 13.3 | 16.7 |

The in-vitro model used according to Tanojo (J. Control Rel. 45 (1997) 41-47) has proven to be an excellent model in which the in-vitro flux rates measured correlated outstandingly with the in-vivo flux rates, which were measured in several clinical studies. The result of this is that the therapeutically desired daily flux rates of active ingredient of a minimum 3 mg, for example, 3-15 mg, preferably of 4-12 mg or 6-12 mg can be achieved through use of the inventive TTS.

Figure 3:
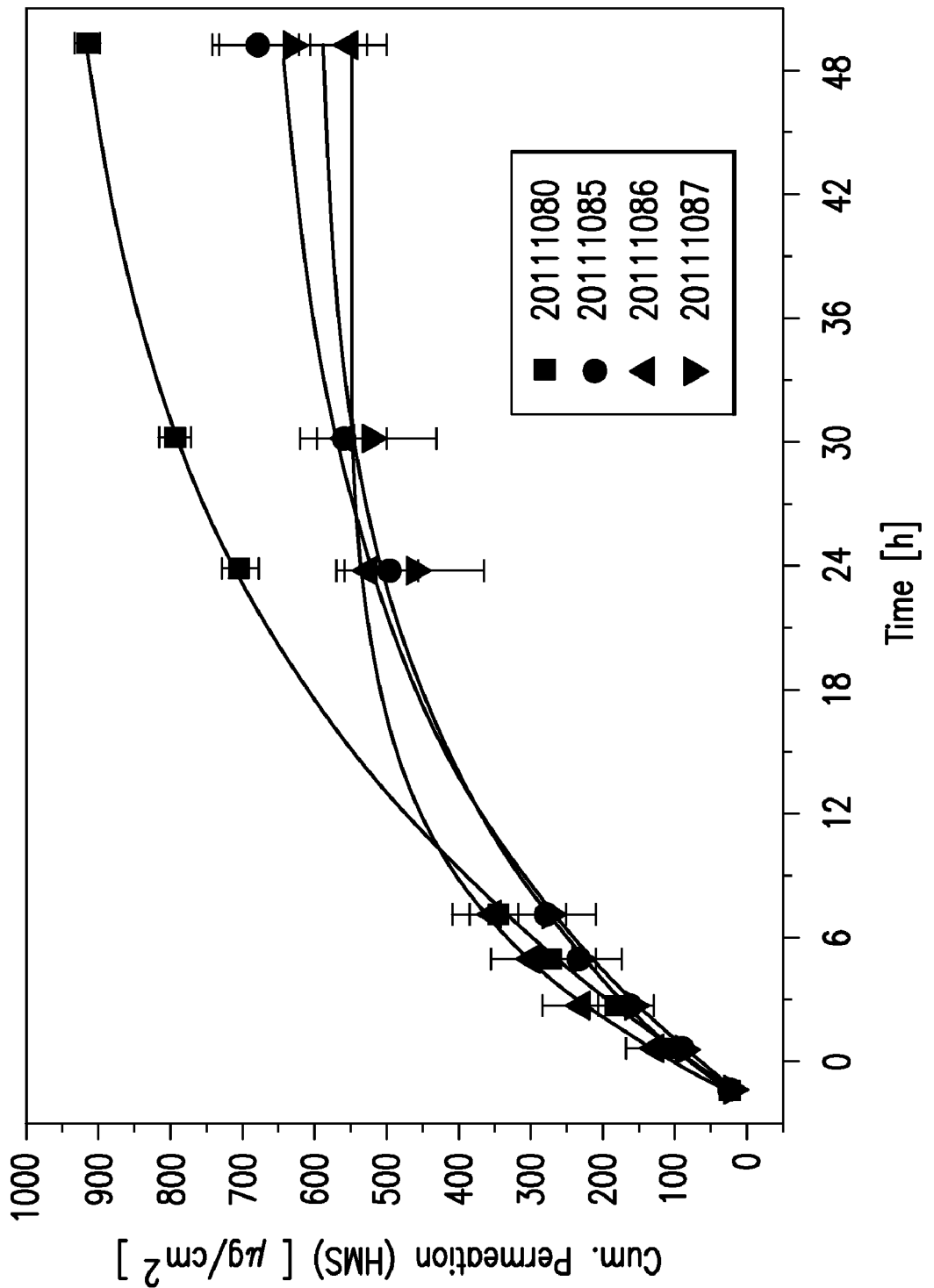
FIG. 3 illustrates the in-vitro flux rate through mouse skin for the high purity free base of fesoterodine.

Flux rates of fesoterodine (high purity free base) through mammalian skin comparable to in-vitro could be achieved from acrylate and silicone based matrices as well (FIG. 3, Table 2).

Therefore in one form of execution the invention concerns the use of a free base of the general Formula I,

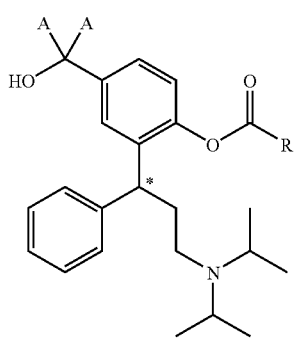

Formula I in which A is hydrogen or deuterium, R stands for a group that is selected from $C_{1-6}$-alkyl, $C_{3-6}$-cycloalkyl or phenyl, which may each be substituted with $C_{1-3}$-alkoxy, fluorine, chlorine, bromine, iodine, nitro, amino, hydroxyl, oxo, mercapto or deuterium and where the C-atom marked with a star "*" may be present in the (R)-configuration, the (S)-configuration or as a mixture of it and whereby the free base is present in a purity of above 97 percent by weight minimum, preferably above 98 percent by weight, especially preferably above 98.5 percent by weight and notably especially preferably above 99 percent by weight, for manufacture of a medicine for transdermal delivery, characterized by the fact that the compound of the general Formula I is introduced into a polymer layer, preferably into a self-adhesive polymer layer and that the medicine a compound of the general Formula I is released in a daily dose of 0.5 mg-20 mg/day, preferably of at least 3 mg/day, for example, 3-15 mg/day, preferably 4-12 mg/day and notably especially preferably 6-12 mg/day through the skin of a mammal, in particular through human skin.

In a preferred form of execution of the invention the compound of the general Formula I where R is selected out of the methyl, ethyl, 1-propyl, isopropyl (i-Pr), 1-butyl, 2-butyl, tertiary-butyl, iso-butyl, pentyl and hexyl group, whereby it is especially preferred that R be an isopropyl and whereby it is especially preferred that the C-atom identified with "*" be present in the (R)-configuration, is used for the manufacture of the above named drugs.

In particularly preferred forms of execution the medicine contains the high purity base of fesoterodine as the active ingredient.

In a particularly preferred form of execution the invention therefore concerns the use of a high purity compound of the general Formula I used for the manufacture of a medicine, whereby the medicine
(a) comprises a self-adhesive polymer matrix that contains the high purity base of fesoterodine and
(b) delivers high purity base of fesoterodine with a flux rate of 0.5-20 mg/day, preferably of at least 3 mg/day, for example, 3-15 mg/day, especially preferably 4-12 mg/day through human skin.

As FIG. 2 shows, the delivery of the active ingredient from such drugs is largely constant over a minimum 24 hours following an initial burst effect phase.

Therefore, in a different special form of execution the invention concerns the use of a high purity combination of the general Formula I, for example, fesoterodine for the manufacture of a medicine, whereby the medicine after an initial burst effect phase releases the solution of the general Formula I over a minimum of 24 hours, preferably over a minimum of 36 hours at a constant flux rate.

In this patent application the expression "steady-state" is understood to mean a dynamic equilibrium that adjusts itself after an initial lag phase following application of the inventive device for the first time.

"Steady-state flux rate" is understood to mean a flux rate that adjusts after the initial lag phase.

In this patent application the expression "constant flux rate" is understood to mean a steady-state flux rate in the case of which a compound of the general Formula I is transported at an average flux rate through human skin, which exhibits an intra-individual variability CV over the time of a maximum of 30%, preferably a maximum of 20% where CV is determined according to the equation $CV=(sd:x)\times100\%$ (see the Cawello (ED) calculation in "Parameters for Compartment-free Pharmacokinetics", Shaker Verlag, Aachen, 1999, Page 112). In the course of this a daily dose is administered at an average flux rate of daily dose: 24 (mg/hour) with a CV of 30%. To the skilled person it is clear that a steady flux rate is only adjusted following an initial burst effect phase ("lag phase") after application for the first time of the device. The lag phase is therefore not taken into consideration in the calculation of the steady flux rate.

In this patent application, unless expressly stated otherwise, the expression "flux rate through human skin" is understood to mean a flux rate that was measured according to Tanojo in an in-vitro human skin model as described in Example Execution 3.2.

The preferred polymer matrices are self-adhesive polymer matrices of the EVA-, SXS, silicone or acrylate type, the properties and manufacture of which are described in more detail in the following:

Silicone Adhesives:

The preferred silicone adhesives are amine resistant, pressure sensitive, polymeric organosiloxane adhesives.

In most cases silicone contact adhesives represent polymeric dimethylsiloxanes; however in principle other organic residues, such as ethyl or phenyl groups, for example, may also be available instead of the methyl groups. Amine resistant silicone contact adhesives are generally characterized in that they contain not any or only a few free silanol functions because the Si—OH— groups were alkylated. Such adhesives are described in EP 180 377. Condensates or mixtures of silicone resins and polymeric organosiloxane adhesives such as described in US RE 35 474 are especially preferred adhesives.

Suitable adhesives are sold, for example, by Dow Corning as the so-called Bio-PSA adhesives. In the process mixtures of the contact adhesive Bio PSA Q7-4301 and Q7-4201 are particularly suitable, especially in a 40:60 to 60:40 ratio.

Patch matrices based on silicone adhesives are processed predominantly in solvent based procedures. For this purpose a solution of contact adhesives and active ingredient are manufactured in a first step in an organic solvent or a mixture of solvents. In a second step the solution is spread out and laminated, and the solvent is then removed. Such a procedure is described as an example in WO 99/49852.

An alternative procedure that dispenses with the use of organic solvents is the hot melt procedure. In this procedure the polymer or the contact adhesive are melted at temperatures between 70 and 200° C., preferably between 90 and 160° C. and especially preferably between 100 and 150° C. and the active ingredient introduced into the homogenized matrix melt. After brief homogenization the adhesive matrix that contains the active ingredient is cooled again so that the active ingredient is exposed to a thermal load in general for less than 5 minutes, if desired even for 4, 3, and 2 or even for less than 1 minute. Following this the active ingredient is present in the solidified polymer melt. During the process the active ingredient is broadly shielded from critical environmental influences (light, oxygen).

This procedure has the advantage over the solvent based procedure that the high purity bases of the general Formula I are not exposed to any solvent influences but instead are able to be added immediately into the hot melt, where after a short homogenization they are stabilized in the cooling polymer matrix. The hot melt procedure is preferably carried out in an extruder, for example, in a twin screw extruder, as described in WO 99/48493.

At the above mentioned processing temperatures the silicone adhesives are generally too viscous, meaning they have a dynamic viscosity of above 150 Pa's. Various procedures were described in the patent literature to make the viscosity of the silicone adhesives hot-meltable through the admixing of suitable additives (softeners). Examples of those softeners for silicone are glycerol monolaurate or lauryl acetate as described in EP 835 136, waxes of the formula R—C(O)—OR' as described in EP 360 467, alkylmethyl siloxane waxes as described in EP 524 775, siloxanated polyether waxes as described in EP 663 431 or organic waxes as described in US RE 36 754.

Generally speaking the softeners are added to the silicone adhesive in a quantity of 1-30 percent by weight based on the total mixture of the hot-meltable adhesive mixture. The preferred softeners are organic waxes as described in US RE 36 754, for example, ozokerite wax, ceresine wax, paraffin wax, candelilla wax, carnauba wax, beeswax or mixtures of these waxes, where ozokerite and ceresine are absolutely, especially preferred.

Ready-made hot-meltable silicone contact adhesives, in particular mixtures of silicone contact adhesives with ceresine or ozokerite may be obtained at Dow Corning, Mich.

For example, through the addition of 10 percent by weight ceresine wax to a silicone contact adhesive, it was possible to lower the dynamic viscosity of the resulting contact adhesive mixture from above 150 Pa's to below 50 Pa's at a processing temperature of 150° C. Such a silicone based contact adhesive mixture can be processed very well in a temperature range of from 70° C. to 200° C., and in particular in the range between 100° C. and 150° C. in a hot melt procedure.

Surprisingly, it was determined that hot-meltable silicone contact adhesives are excellently suited for the transdermal delivery of the compounds of the general Formula I.

One object of the invention is therefore a device for the transdermal delivery of a compound of the Formula I

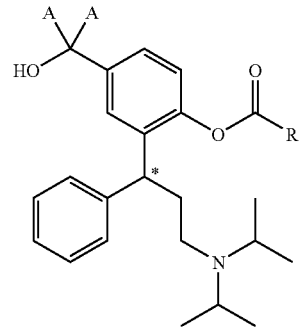

Formula I in which A means hydrogen or deuterium, R stands for a group that is selected from $C_{1-6}$-alkyl, $C_{3-10}$-cycloalkyl or phenyl, which may each be substituted with $C_{1-3}$-alkoxy, fluorine, chlorine, bromine, iodine, nitro, amino, hydroxyl, oxo, mercapto or deuterium and where the C-atom marked with a star "*" may be present in the (R)-configuration, the (S)-configuration or as a mixture of it, characterized by the fact that the compound of the general Formula I was introduced into a polymer layer (adhesive matrix) in the form of a free base, with a degree of purity of above 97 percent by weight, preferably above 98 percent by weight, especially preferably above 98.5 percent by weight and absolutely especially preferably above 99 percent by weight, whereby the adhesive matrix incorporates an amino-resistant silicone.

In an especially preferred form of execution of the invention the adhesive matrix is based on a hot-meltable mixture of a silicone based contact adhesive and at least one softener, in particular an organic wax, for example, ozokerite. In preference the inventive silicone-based matrix was into the high purity base of fesoterodine as the active ingredient.

In the process "hot-meltable" is understood to mean that the adhesive exhibits a dynamic viscosity of at the highest 150, preferably 120 Pa's at the highest, at an accepted working temperature during a hot melt procedure of, for example, 160° C.

A further aspect of the invention is a medicine for the transdermal delivery of a compound of the general Formula I comprising an adhesive matrix that comprises:
(a) 50-99 percent by weight of a contact adhesive mixture consisting of
  (i) 70-99 percent by weight of an amino resistant silicone adhesive,
  (ii) 1-30 percent by weight, preferably 3-15 percent by weight of an appropriate softener, preferably an organic wax, which especially preferably is selected from the group ozokerite wax, ceresine wax, paraffin wax, candelilla wax, carnauba wax, beeswax or mixtures of these waxes where ozokerite wax and ceresine are especially preferred, (b) 1-40 percent by weight of a compound of the general Formula I is introduced into the matrix in the form of the high purity free base.

Silicone adhesives can be bought commercially and are sold, for example, by Dow Corning as Bio-PSA Q7-4300 or Bio-PSA Q7-4200. Hot-meltable silicone adhesives incorporating mixtures of PSA 7-4300 with organic waxes like ozokerite or ceresine are also obtainable from Dow Corning.

FIG. 3/4 shows the in-vitro flux through mouse skin that was achieved using a silicone based patch manufactured in a hot melt procedure that contains ozokerite as a softener for the adhesive matrix and that contains the high purity free base of fesoterodine in the adhesive matrix.

EVA-Adhesives

EVA adhesives are hot-meltable contact adhesives, which are based on ethylene vinyl acetate-copolymers ("EVA-contact adhesive"). EVA-adhesives such as these are described in U.S. Pat. No. 4,144,317 for example. EVA-adhesives feature good adhesive properties, simple manufacture and processing as well as good skin compatibility. EVA-adhesives can be obtained, for example, at Beardow Adams (13/BA).

What was said under silicones essentially applies for the processing in a hot melt procedure where no softeners have to be added to the EVA-contact adhesives.

One object of the invention is therefore a device for the transdermal delivery of a compound of the Formula I

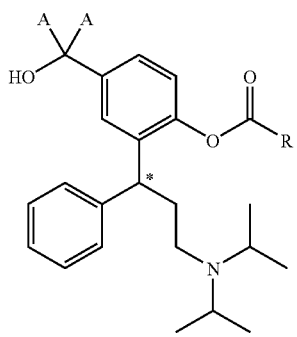

Formula I in which A means hydrogen or deuterium, R stands for a group that is selected from $C_{1-6}$-alkyl, $C_{3-10}$-cycloalkyl or phenyl, which may each be substituted with $C_{1-3}$-alkoxy, fluorine, chlorine, bromine, iodine, nitro, amino, hydroxyl, oxo, mercapto or deuterium and where the C-atom marked with a star "*" may be present in the (R)-configuration, the (S)-configuration or as a mixture of it, characterized by the fact that the compound of the general Formula I was introduced into a self adhesive polymer layer (adhesive matrix) in the form of a free base, with a degree of purity of over 97 percent by weight, preferably above 98 percent by weight, especially preferably above 98.5 percent by weight and notably especially preferably above 99 percent by weight, whereby the adhesive matrix comprises an adhesive of the EVA type.

In an especially preferred form of execution of the invention the EVA-based adhesive matrix has been manufactured in a hot melt procedure. In preference the inventive EVA-based matrix was introduced into the high purity base of fesoterodine as the active ingredient.

FIGS. 2 and 3 illustrate the in-vitro flux rates through human skin and mouse skin respectively, that were achieved using an EVA-based patch manufactured in a hot melt procedure that contains the high purity base of fesoterodine in the adhesive matrix.

SxS-Contact Adhesives

SxS contact adhesives may be processed in both solvent based manufacturing procedures and hot melt procedures. In this patent application the term "SxS contact adhesives" is understood to mean styrene block copolymer based adhesives that carry non-elastomeric styrene blocks at the ends and elastomeric blocks in the middle. The elastomeric blocks may, for example, consist of polyethylene butylene, polyethylene propylene, polybutadiene, polyisobutylene or polyisopropene.

Suitable SxS adhesives are described in U.S. Pat. No. 5,559,165 or U.S. Pat. No. 5,527,536 for example and feature good adhesive properties, simple manufacture and processing as well as good skin compatibility.

SxS contact adhesives may be obtained both commercially (e.g. as Duro Tak 378-3500 at National Starch & Chemical) and manufactured for oneself using hot melt extrusion equipment during the production of patches containing an active ingredient.

For instance, for this purpose appropriate amounts (of the following components at a minimum) of a styrene block copolymer (e.g. Shell Kraton GX1657 or Kraton D-1107CU) are dosed into the extruder with an aliphatic and/or aromatic resin (e.g. Keyser Mackay Regalite R1090 or Regalite R1010 or Regalite R1100) and an oil (e.g. Shell Ondina 933 or Ondina 941) from the individual dosing stations, mixed there and melted. In the last step the active ingredient is dosed into the contact adhesive manufactured in this way in the extruder and the paste laminated on foil sheets. Typical exemplary parts by weight:polymer:resin:oil are e.g. 100:120:20 or 100:200:50. The properties of the SxS contact adhesives can be adapted to the desired properties of the TTS (adhesive strength, minimum cold flow, duration of adherence, releasing profile of the active ingredient etc.) by varying these proportions of amounts.

One object of the invention is therefore a device for the transdermal delivery of a compound of the Formula I

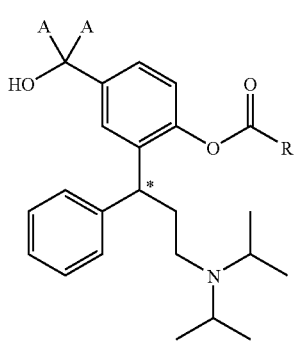

Formula I in which A means hydrogen or deuterium, R stands for a group that is selected from $C_{1-6}$-alkyl, $C_{3-10}$-cycloalkyl or phenyl, which may each be substituted with $C_{1-3}$-alkoxy, fluorine, chlorine, bromine, iodine, nitro, amino, hydroxyl, oxo, mercapto or deuterium and where the C-atom marked with a star "*" may be present in the (R)-configuration, the (S)-configuration or as a mixture of it, characterized by the fact that the compound of the general Formula I was introduced into a self-adhesive polymer layer (adhesive matrix) in the form of a free base, with a degree of purity of over 98 percent by weight, preferably above 97 percent by weight, preferably above 98 percent by weight, especially preferably above 98.5 percent by weight and absolutely especially preferably above 99 percent by weight, whereby the adhesive matrix incorporates a contact adhesive on an SXS-basis.

In an especially preferred form of execution of the invention the SXS-based adhesive matrix has been manufactured in a hot melt procedure. In preference the inventive SXS-based matrix was introduced into the high purity base of fesoterodine as the active ingredient.

FIGS. 2 and 3 illustrate the in-vitro flux rates through human skin and mouse skin respectively, that were achieved using an SXS-based patch manufactured in a hot melt procedure into which the high purity free base of fesoterodine was introduced.

Due to the potential oxidative effect of the SXS adhesives, antioxidants are preferably added to SXS-based adhesive matrices. An example for a commercially obtainable, suitable antioxidant is Irganox® (CIBA).

Acrylate Adhesives:

Polyacrylates are produced through the radical polymerization of (meth) acrylic acid derivates, whereby other suitable compounds, such as vinyl acetate, for example, may be used as other monomers. The expression "polyacrylate" in this patent application includes polymers that comprises units that are based on acrylic acids and/or meth-acrylic acids as well as copolymers and mixtures of them.

As a matter of principle, in the selection of appropriate monomers the resulting contact adhesives can be constituted in such a way that they exhibit specific properties, meaning a favorable solvent capacity for the active ingredient, a desired movability of the active ingredient in the matrix as well as a desired transfer-rate through the skin. The transfer rate is significantly limited by the distribution coefficients and the resorption of the active ingredient through the skin.

The pressure sensitive contact adhesive of the polyacrylate type may be a homopolymer and/or copolymer of at least one acrylic acid and/or meth-acrylic acid derivative in the form of a solution in an organic solvent. The polyacrylate type contact adhesive may be cross-linkable or non-cross-linkable. The cross-linking reagent links the polymer chains using reactive groups. This may result in an increased cohesion of the contact adhesive.

Preferably the polymer contact adhesive of the polyacrylate type consists of the following monomers at a minimum: Acrylic acid, acrylamide, hexyl-acrylate, 2-ethyl-hexyl-acrylate, hydroxy-ethyl-acrylate, octyl-acrylate, butyl-acrylate, methyl-acrylate, glycidyl-acrylate, methyl-acrylate, meth acrylic acid, methacrylamide, hexyl-methacrylate, 2-ethyl-hexyl amide-acrylate, octyl-methacrylate, methyl-methacrylate, glycidyl-methacrylate, vinyl acetate, vinyl pyrrolidon, allyl-acrylate.

The polymer contact adhesives of the acrylate type, cross-linkable contact adhesives that are polymerized from a combination of the following monomers are preferred:
2-ethyl-hexyl-acrylate/N-butyl-acrylate/butyl-acrylate/acrylic acid,
2-ethyl-hexyl-acrylate/N-butyl-acrylate/vinyl acetate/acrylic acid,
2-ethyl-hexyl-acrylate/vinyl acetate/acrylic acid,
2-ethyl-hexyl-acrylate/vinyl acetate/allyl-acrylate,
2-ethyl-hexyl-acrylate/vinyl acetate/divinyl-benzol/acrylic acid,
2-ethyl-hexyl-acrylate/vinyl acetate/allyl-methacrylate/acrylic acid,
2-ethyl-hexyl-acrylate/vinyl acetate/2-hydroxy-ethyl-acrylate,
2-ethyl-hexyl-acrylate/vinyl acetate/2-hydroxy-ethyl-methacrylate,
2-ethyl-hexyl-acrylate/fumaric acid-diethyl-ester/acrylic acid,
2-ethyl-hexyl-acrylate/maleic acid-diethyl-ester/2-hydroxy-ethyl-acrylate.

The following compounds can be named as preferred cross-linking preparations: Diphenyl-methane-4-diisocyanate, hexamethylene-diisocyanate, titanium-acetyl acetonate, aluminum-acetyl acetonate, ferrous-acetyl acetonate, zinc-acetyl acetonate, magnesium-acetyl acetonate, zirconium-acetyl acetonate, 2-ethyl-1,3-hexanediol-titanate, tetra-isooctyl-titanate, tetra-nonyl-titanate, polyfunctional propylene-imine-derivate, ether-derivate from melamine-formaldehyde-resin, high methylated urethane-resin, imine-melamine-resin.

The non-cross linkable contact adhesives may be polymerized, preferably from a combination of the following monomers:
2-ethyl-hexyl-acrylate/N-butyl-acrylate/vinylacetate,
2-ethyl-hexyl-acrylate/vinylacetate,
2-ethyl-hexyl-acrylate/N-butyl-acrylate/vinylacetate/allyl-acrylate,
2-ethyl-hexyl-acrylate/N—N-butyl-acrylate/allyl-methacrylate,
2-ethyl-hexyl-acrylate/N-butyl-acrylate/vinylacetate/divinyl-benzol,
2-ethyl-hexyl-acrylate/fumaric acid-diethyl-ester/allyl-acrylate,
2-ethyl-hexyl-acrylate/maleic acid-diethyl-ester/allyl-acrylate,
2-ethyl-hexyl-acrylate/N-butyl-acrylate/acrylamidemnylacetate/allyl-acrylate,
2-ethyl-hexyl-acryate/N-butyl-acrylateiso-butyl-acrylate/vinylacetate/allyl-acrylate.

Furthermore a few contact adhesives may be used in the form of an aqueous dispersion (the dispersive type). The usage of these dispersive type contact adhesives may bring the advantage that no inflammable or toxic solvents become vaporized during the coating and drying.

Dispersive type contact adhesives may be polymerized preferably from a combination of the following monomers:
N-butyl-acrylate/iso-butyl-acrylate/acrylic acid.
2-ethyl-hexyl-acrylate/N-butyl-acrylate/acrylic acid,
2-ethyl-hexyl-acrylate/N-butyl-acrylate/2-hydroxy-ethyl-acrylamide,
2-ethyl-hexyl-acrylate/N-butyl-acrylate/vinyl acetate/acrylamide,
2-ethyl-hexyl-acrylate/N-butyl-acrylate/vinyl acetate/2-hydroxy-ethyl-acrylate,
2-ethyl-hexyl-acrylate/N-butyl-acrylate/allyl-acrylate/acrylic acid,
2-ethyl-hexyl-acrylate/N-butyl-acrylate/vinyl acetate/divinyl-benzol.

Suitable polyacrylates for use in this invention are cross-linked by multivalent metal ions in order to improve the physical properties of the contact adhesive or in order to adapt it to the specific requirements. The metal ions are normally applied in the form of metal chelate compounds, which are soluble in organic solvents. Especially suitable cross-linking agents are aluminum acetyl acetonate and titanium acetyl acetonate.

If the contact adhesive used in compliance with this invention is a polyacrylate contact adhesive, the solubility capacity generally depends on the type and the quantity of the free functional groups in the contact adhesive.

The most preferred contact adhesives for use in the device of this invention are the polyacrylates with polar groups, in particular with the free hydroxy groups. Examples of such contact adhesives are the polyacrylates for the manufacture of which polar monomers, such as e.g. hydroxy-ethyl-acrylate, hydroxy-ethyl-methacrylate, acrylic acid or methacrylic acid are used in an amount of approximately 1-10% (w/w), especially preferably in a quantity of 3-8% (w/w), absolutely especially preferably in an amount of 4-6% (w/w). Such contact adhesives are obtainable commercially under the brand name Duro-Take® (National Starch & Chemicals; Hamburg).

Notably, especially preferred for use in the device of this invention are the contact adhesives of the polyacrylate type, where hydroxy-ethyl-acrylate and/or hydroxyl-ethyl-methacrylate monomers are admixed during polymerization in a quantity of 3-8% (w/w), notably especially preferably in a quantity of 4-6% (w/w).

Such a contact adhesive may be obtained according to the general procedure that is described in U.S. Pat. No. 5,498,418 as follows: The contact adhesive can be obtained through radical polymerization. In a first step a mixture consisting of 21 to 40 percent by weight vinyl acetate, 55-70 percent by weight of an acrylic acid $C_{2-8}$-alkyl ester and 3 to 10 percent by weight of an acrylic acid $C_{2-4}$ hydroxyl acrylic ester is manufactured in an organic solvent with 100 percent by weight monomers in the mixture.

In a second step a conventional cross-linked agent in an organic solvent and—optionally—the active ingredient of the quality required in the transdermal device (patch) for the intended usage is admixed, if necessary in an organic solvent.

Finally, in a third step the mixture of the particular acrylate vinyl acetate copolymer obtained is cross-linked in an additional step, conducted through heating and through the removal of the organic solvent or the mixture of solvents used. The active ingredient obtained is "built into" the contact adhesive substance in a special way through the successive and additional cross-linking of the special acrylate vinyl acetate copolymer.

Alternatively the acrylate vinyl acetate copolymer can be polymerized and cross-linked in the absence of the active ingredient. The active ingredient is then added during the application of the acrylate vinyl acetate copolymer when the patch is manufactured. The acrylate vinyl acetate copolymer has a relative viscosity of 3.0 to 4.2 at 20° C.

Preferably the mixture contains 2-ethyl hexane acrylate and hydroxyl ethyl acrylate monomers in addition to vinyl acetate. Preferably the subsequent cross-linking of the special acrylate vinyl acetate copolymers is performed with a titanium acid ester consisting of polybutyl-titanate and/or titanium acetyl acetonate, preferably in a quantity of 0.3 to 3 percent by weight proportional to the weight of the copolymer.

The following steps can cover a process for the manufacture of a TTS in compliance with this invention: As a first step the manufacture of a solution of a copolymer, in which the active ingredient, in the amount required for the intended use of the TTS as well as a conventional cross-linker or a mixture of it, is optionally contained, and whereby the copolymer is obtained through the radical polymerization of a mixture of monomers consisting of 21 to 40 percent by weight vinyl acetate, 55 to 70% by weight of an acrylic acid-$C_{2-8}$ alkyl ester and 1 to 10 percent by weight of an acrylic acid-$C_{2-4}$ hydroxy alkylester, the coating of the above named solution in the layer thickness required on the protective film of the TTS and the removal of the solvent or the mixing of the solvents by heating, which results in an additional cross-linking of the special acrylate vinyl acetate copolymer.

One form of execution of such a process is characterized by the fact that the acrylate vinyl acetate copolymer—optionally—the active ingredient and the cross-linkable agent are dissolved at the start in a solvent, which contains 20 to 40 percent by weight ethanol or an ethanol methanol mixture, with a ratio of solid components consisting of 40 to 60 percent by weight of the mixture of the special acrylate vinyl acetate copolymer of the cross-linkable agent and the active ingredient.

In a different—preferred—form of execution of the invention the active ingredient is only added to the dispersion after crosslinking of the acrylate, which is then spread on the protective film following homogenization.

A particular example of execution for the preparation of such an acrylate-vinyl acetate contact adhesive is published in U.S. Pat. No. 5,498,418, column 2, lines 61 to column 3, line 10, quoted here as a reference.

A particularly preferred contact adhesive for use in this invention are the commercially available contact adhesives Duro-Tak® 387-2287 and Duro-Tak® (3)87 (National Starch & Chemicals; Hamburg). In an especially preferred form of execution of the invention the Duro-Tak contact adhesive is mixed in an appropriate solvent with the desired amount of the active ingredient and the resulting homogenous dispersion spread out in the thickness desired. Finally the solvent or the mixture of solvents is removed at raised temperatures (50-70° C.).

One object of the invention is therefore a device for the transdermal delivery of a compound of the Formula I

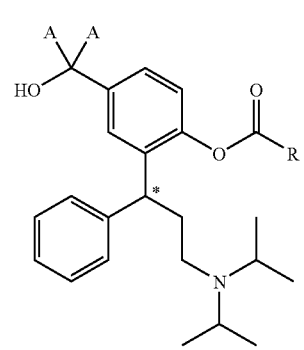

Formula I in which A means hydrogen or deuterium, R stands for a group that is selected from $C_{1-6}$-alkyl, $C_{3-10}$-cycloalkyl or phenyl, which may each be substituted with $C_{1-3}$-alkoxy, fluorine, chlorine, bromine, iodine, nitro, amino, hydroxyl, oxo, mercapto or deuterium and where the C-atom marked with a star "*" may be present in the (R)-configuration, the (S)-configuration or as a mixture of it, characterized by the fact that the compound of the general Formula I was introduced into a polymer layer, preferably a self-adhesive polymer layer (adhesive matrix) in the form of a free base, with a degree of purity of above 97 percent by weight, preferably above 98 percent by weight, especially preferably above 98.5 percent by weight and notably especially preferably above 99 percent by weight, whereby the polymer layer incorporates at least one polymer of the acrylate and/or methacrylate type.

In preference the high purity base of fesoterodine as the active ingredient was introduced into the inventive acrylate-based matrix.

FIG. 3 shows the in-vitro flux rates through mouse skin that were achieved with an acrylate based patch manufactured in a hot melt procedure in which the high purity free base of fesoterodine was introduced into the adhesive matrix.

Auxiliary Agents and Additives

The above described polymer matrices of the transdermal devices containing an active ingredient in compliance with the invention may contain other auxiliary agents and additives. Examples are buffers, solutizing agents, chemical stabilizers, antioxidants, other auxiliary agents for retarding as well as skin penetration enhancers.

Skin penetration enhancers may be added, for example, to enlarge the amount of active ingredient that permeates through the skin or to shrink the application area of the device. Non-limiting examples of common penetration enhancers are alcohols, in particular short chained alcohols such as ethanol, fatty alcohols, e.g. lauryl alcohol, polyalcohols such as glycerin, amides, e.g. aromatic amides like N,N-diethyl-m-toluamide, amino acids, azones, oils like menthol or peppermint oil; fatty acids and their esters like oleic acids, lauryl acids, isopropyl myristate or glycerol monolaurate; macrocycles such as for example, cyclopentadecanon; phospholipides such as lecithin for example; 2-pyrrolidones, sulfoxides such as dimethyl sulfoxide for example.

On account of the good penetration properties of the free bases of the general Formula I, forms of execution of the invention are preferred in which the addition of an enhancer is dispensed with.

A hydrophilic component such as a hydrophilic polymer for example, may be added to the adhesive matrix as another component. These hydrophilic polymers may serve as solubility facilitators or crystallization inhibitors for the compounds of the general Formula I and contribute to a uniform distribution of the active ingredient in the adhesive matrix.

Appropriate hydrophilic polymers for use in the TTS in compliance with the invention may, for example, be chosen from the group of the polysaccharides, substituted polysaccharides, polyethylene oxides, polyvinyl acetates, polyvinyl pyrrolidones (PVP), PVP with appropriate softeners, polyethylene glycols, polypropylene glycols, polyacrylates, copolymers from polyvinyl pyrrolidone and (poly)vinyl acetate, copolymers from ethylene and vinyl acetate as well as polyvinyl alcohols with a suitable softener, for example, glycerin.

Preferred hydrophilic polymers are PVP, polyethylene oxide (PEO), polyvinyl acetate (PVAc) as well as copolymers from PVP and vinyl acetate.

The hydrophilic polymers may be added to the adhesive layer, for example, in a portion of 0.5-40 percent by weight based on the total weight of the adhesive layer. Preferably 2-25 percent by weight, especially preferably 2-15 percent by weight of 2-10 percent by weight hydrophilic polymers are added.

Those hydrophilic polymers that exhibit a dynamic melting viscosity of a maximum 150 Pa's, preferably less than 120 Pa's and especially preferred below 80 Pa's, at temperatures below 170° C. are especially suitable for use in a hot melt procedure. A suitable softener, for example, glycerin, is eventually to be added beforehand if the dynamic viscosity of the hydrophilic polymer is too low at the desired processing temperature.

The addition of the above-named hydrophilic polymers may be advantageous, particularly in the case of very hydrophobic adhesive matrices, for example, silicone, polyisobutylene or SXS matrices.

As already described in WO 01/35957, the free bases of the 3,3-diphenylpropylamine-monoester tend towards a drop in concentration, for example, as a result of hydrolysis and interchange esterification. It was then surprisingly determined that the 3,3-diphenylpropylamine-monoesters can be stabilized significantly in matrices with hydrophilic constituent parts.

While, for example, the free base of fesoterodine is decomposed as an oil after storage for 6 months at 5° C. to around 3-4%, a drop in concentration cannot be established or only established essentially to a lesser extent when fesoterodine is incorporated in matrices, which contain polar components.

Examples for these such matrices, which lead to the stabilization of the monoester of the general Formula I are matrices, for example, that contain polyacrylates, in particular polyacrylates with polar groups, EVA or mixtures of silicone adhesives with hydrophilic polymers, for example, PVP or PEO, (Table 4).

TABLE 4

Stabilization of fesoterodine in various matrices during storage

| Matrix | 5° C. Stabilization Factor[1] | 25° C./60% RH Stabilization Factor[1] | Production procedure |
|---|---|---|---|
| EVA | 7-fold | 4.5-fold | Hot melt |
| Silikon/Cer[3] | — | — | Hot melt |
| Silicone + 2% PVP | 2-fold | 2-fold | Solvent |
| Silikon/Cer[3] + 5% PEO | 3-fold | 2.5-fold | Hot melt |
| Polyacrylate | No decomposition detectable[2] | 13-fold | Solvent |
| PIB | — | — | Solvent |
| SXS | — | 1.1-fold | Hot melt |

[1]The stabilization factor was determined by the division of the average monthly drop in concentration of the fesoterodine base during storage as a raw material (oil) by the average monthly drop in concentration during storage in matrices;
[2]until the end of the period of measurement after 6 months;
[3]Cer = Ceresine As Table 4 shows, the incorporation of fesoterodine in matrices consisting of EVA adhesives, polyacrylate adhesives or mixtures of silicone adhesives with hydrophilic polymers such as PEO or PVP leads to a distinct stabilization of the fesoterodine and is independent of the manufacturing process (the hot melt or the solvent procedure).

One form of execution of the invention therefore concerns matrices or pharmaceutical formulations or devices in which the compounds of the general Formula I as a free base are subject to a slower drop in concentration than is the case if the free base is stored under identical conditions, not embedded in a polymer as an oil. Preferred forms of execution are those which at 5° C. and/or at 25° C. lead to a 2-, 3-, 7- or 10-fold stabilization of the 3,3-diphenylpropylamine monoester by comparison with storage as a free base. Especially preferred pharmaceutical formulations or devices in compliance with the invention are those in which the free base is present in a polymer layer, in which a drop in concentration of a compound of the general Formula I of less than 3%, preferably of less than 2% or 1% in the case of 6-month storage at 4° C. and of less than 10%, preferably less than 5% and especially preferably less than 3% or 1.5% in the case of 3-month storage at 25° C. and 60% atmospheric moisture occurs.

Preferred matrices are those which contain 50-95 percent by weight of an contact adhesive that is chosen from the group of the Acrylate adhesives as well as their copolymers, in particular acrylate adhesives with polar groups, for example with free hydroxy groups, EVA-adhesives Silicone adhesives which contain 2-25 percent by weight, preferably 2-10 percent by weight of a hydrophilic polymer, in particular chosen from PEO, PVP or PVAc, SXS- or PIB adhesives which contain 2-25 percent by weight, preferably 2-10 percent by weight of a hydrophilic polymer, Mixtures of hydrophilic contact adhesives (e.g. polar polyacrylates) with hydrophobic contact adhesives (e.g. silicone, SXS or PIB adhesives).

Notably especially preferred contact adhesives for the manufacture of the matrices in compliance with the invention are polyacrylates, in particular those with polar groups. These matrices exhibit both an excellent releasing profile for fesoterodine and outstanding stabilization properties for 3,3-diphenyl propylamine monoesters.

Based on experience surfaces up to maximum TTS sizes of approximately 50 cm$^2$ are accepted by patients. The size of the TTS is typically up to 40 cm$^2$, preferably sizes are between 5 and 35 cm$^2$ and especially preferably between 10 and 30 cm$^2$.

The matrix weight of the TTS typically varies between 30 and 300 g/m$^2$, whereby the matrices with a weight of 40-200 g/m$^2$ and especially 40-150 g/m$^2$, are preferred.

The loading of the active ingredient depends on the absorption/liberation capacity of the respective matrix for the active ingredient as well as on the manufacturing procedure. Generally speaking the loading rate of the active ingredient makes sense between 5 and approximately 40 percent by weight based on the total weight of the matrix containing the active ingredient whereby the lower maximum loading rates between 7 and 30 percent by weight are preferred, and in particular between 8 and 20 percent by weight for the manufacture of a 1-3 day TTS. If a medicine is to be manufactured for a 7-day administration of a compound of the general Formula I, then comparatively higher active ingredient concentrations above, for example, 15-40 percent by weight are used.

A loading of active ingredient (mg/cm$^2$ matrix base) of 0.1-12, preferably 0.25-7.5, especially preferably from 0.3 to 4 and notably especially preferably of 0.6 to 2.6 results. In the case of devices for a 7-day application the loading lies preferably at a minimum of 2 mg/m$^2$.

Another object of the invention is a method as a prevention and/or treatment of incontinence, hyperactivity of the detrusor, hyperactivity of the bladder, pollakisuria, nocturia or imperative urinary urgency through the administration of a compound of the general Formula I as a free base, and with the degree of purity in compliance with the invention as described in the above, on a mammal, in particular on a person, who requires the prevention against or the treatment of the above named diseases.

The following examples serve for further illustration of the invention.

EXAMPLE EXECUTIONS

1. Manufacture of the High Purity Free Base of Fesoterodine

A. Manufacture of the Fesoterodine Base (B, see FIG. 1, R=i-Pr)

Drops of a solution of 18.6 g isobutyric acid chloride in 250 ml dichloromethane were added in approximately 10 minutes to a solution of 59.8 g (175.1 mol) (R)-2-[3-(diisopropylamino)-1-phenylpropyl]-4-(hydroxymethyl)phenol cooled to −3° C. (A, see FIG. 1) dissolved in 750 ml dichloromethane with agitation and cooling by ice bath. A white substance precipitated after approximately 5 minutes. For this purpose drops of a solution of 17.7 g triethylamine in 250 ml dichloromethane were added in 5 minutes under agitation and ice bath cooling. The batch was washed once with each of 250 ml water, 250 ml approximate 5% aqueous NaHCO$_3$ solution and 250 ml water. The dichloromethane extract dried over Na$_2$SO$_4$ was evaporated to a low small bulk on a rotary evaporator to constant weight, whereby a pale yellow, high viscosity oil was left.

Raw yield: 63.7 g (88.5% of the theory).

The purity of B in the HPLC in this example amounted to 94.1%. Typical range for B: 90.5%-94.4% 0.4%. Decomposition occurred in the case of the high vacuum distillation trial with the formation of A and C.

B. Manufacture of the Fumarate Salt (E; FIG. 1; R=i-Pr, X$^-$=Hydrogen Fumarate) of Fesoterodine A solution of 41.87 g (102 mmol) (R)-2-(3-diisopropylamino-1-phenylpropyl)-4-hydroxymethylphenyl isobutyric acid ester (B) in 90 ml 2-butanon was laced with fumaric acid (11.81 g, 102 mmol) with heating. Cyclohexane (20-30 ml) was slowly added with agitation until the onset of clouding after dissolving of the acid. The colorless, homogenous batch was initially left for 18 hours at room temperature and then for several more hours at 0° C. The precipitated, colorless crystals were suctioned off, washed with a little cyclohexane/2-butanon (90:10, percent by volume) and vacuum dried at 30° C.

Yield: 44.6 g (83.1% of the theory) of the hydrogen fumarate salt (E) of the (R)-2-(3-Diisopropylamino-1-phenylpropyl)-4-hydroxymethylphenyl isobutyric acid ester in the form of colorless small plates Melting point: 98.8° C., a second crystallization from the same mixture of solvents yielded the product with a melting point of 103° C.

$[\alpha]_D^{20}$=+6.0 (c=1.0, ethanol); −19.3 (c=1.0, acetonitrile).

$^1$H-NMR (CDCl$_3$): among other things 6.84 ppm for C$\underline{H}$=C$\underline{H}$ from hydrogen fumarate anion.

$^{13}$C-NMR (CDCl$_3$): among other things 135.58 ppm and 170.56 ppm for olefin- and carbonyl carbon from the hydrogen fumarate-anion.

The purity in this example at E (determined with HPLC) amounted to 99.2%.

C. Manufacture of the High Purity Fesoterodine Base (B; FIG. 1, R=i-Pr)

250 g (0.474 mol) crystalline (R)-2-[3-(diisopropylamino)-1-phenylpropyl]-4-(hydroxymethyl)-phenyl-2-methylpropanoate-fumaric acid salt (E) was added to 1 liter water with agitation and heated to 30° C. An almost clear solution was present after approximately 30 minutes. 96.0 g sodium hydrogen carbonate was added with agitation in portions in approximately 10 minutes to the solution cooled to room temperature. 1 liter of dichloromethane was added to the almost clear, colorless solution of fesoterodine hydrogen carbonate. After some stirring time at room temperature (strong development of CO$_2$) the dichloromethane phase was cut off and each washed once with 0.2 liters of 5% aqueous sodium hydrogen carbonate solution and then with 0.2 liters of water. The filtered, clear, colorless dichloromethane phase was evaporated to a low small bulk on a rotary evaporator at a bath temperature of approximately 40° C. to a constant weight, whereby in a final step a diaphragm pump vacuum (ultimate vacuum 5 mbar) was applied. In the course of this (R)-2-(3-Diisopropylamino-1-phenylpropyl)-4-hydroxymethylphenyl isobutyric acid chloride (B) remained as an almost colorless, viscous oil.

Yield: 180.6 g (92.6%)

$[\alpha]_D^{20}$=+5. (c=1., ethanol); −6. (c=1., acetonitrile)

NMR (CDCl$_3$): 19.01, 19.95, 20.59, 21.12, 34.28, 36.89, 41.88, 42.32, 43.90, 48.78, 64.68, 122.57, 125.59, 126.16, 126.86, 127.96, 128.54, 136.88, 138.82, 143.92, 147.90, 175.69 (ppm).

In this example the purity in the HPLC amounted to 99.0%. Typical purities lie between 98.7% and 99.5%.

$^1$H- and $^{13}$C-NMR: No resonance peaks detectable for the hydrogen fumarate anion (compare with E). The long-term storage is preferably done in the dark under argon at –20° C.

D. Manufacture of the Hydrogen Carbonate Salt (E, FIG. 1: 1; R=i-Pr, X$^-$=Hydrogen Carbonate)

Fesoterodine (107.7 mg (R)-2-(3-Diisopropylamino-1-phenylpropyl)-4-hydroxymethylphenyl isobutyric acid ester, B) is covered with a layer distilled water and stirred at room temperature. After two days of stirring, the reaction batch remains unchanged two-phase. No organic material (B or E) could be detected by thin layer chromatography in the aqueous phase at the top (silica gel, solvent system petroleum ether/acetone/triethylamine, 70/20/10 percent by volume).

A slight flow of carbon dioxide gas is fed into the second phase reaction batch at room temperature with agitation. After two days the lower oil phase (fesoterodine) has dissolved totally and clearly in the aqueous phase.

$^{13}$C-NMR-spectrum of the hydrogen carbonate salt of fesoterodine (δ-values):
14.11, 15.36, 15.51, 29.32, 31.09, 38.95, 43.31, 52.38, 60.45, 120.04, 124.07, 124.33, 124.83, 126.12, 131.97, 136.55, 139.06, 144.60, 157.46 (HCO$_3^-$), 175.75.

A good conformity with the $^{13}$C-NMR-spectrum of the hydrochloride of fesoterodine, manufactured through the dissolution of the base in 1 M aqueous hydrochloric acid (δ-value):
13.26, 15.32, 15.48, 29.29, 31.06, 38.95, 43.34, 52.42, 60.49, 120.10, 124.18, 124.38, 124.85, 126.13, 131.97, 136.50, 139.02, 144.61, 175.94.

2. Manufacture of the TTS Matrices 2.1. Manufacture of a Silicone Based Matrix in a Hot Melt Procedure 8.5 g of a silicone based contact adhesive mixture from the silicone adhesive Bio-PSA 7-4300 (Dow Corning, Mich.) was heated to 150° C. with 5 percent by weight ozokerite or ceresine (obtainable from Dow Corning) for around 20 minutes until a homogenous melt came into being 1.5 g fesoterodine (high purity free base) was added and the mixture kept for a further 5 minutes at 150° C. The mixture was then homogenized by hand and laminated onto a pre-warmed foil (120° C., gap width 250 µm). 5 cm$^2$ pieces were cut out for the releasing tests.

2.2. Manufacture of an Acodate Based Matrix in the Solvent Procedure 1.5 g high purity fesoterodine base was dissolved in dichloromethane and added to a solution of 8.5 g Duro-Tak® 387-2287 (in ethyl acetate). The resulting mixture was stirred until a homogeneous dispersion was achieved. The dispersion was then spread out on foil and dried (Erchsen 100 µm, 6 mm sec, drying time: 30 minutes at 50° C.).

2.3. Manufacture of an SXS Based Matrix in a Hot Melt Procedure 100 parts SIS (Kraton D-1107 CU), 150 parts Regalite R 1090, 20 parts Ondina oil and 1 part Irganox were mixed and melted at 140° C., 1.5 g fesoterodine (high purity free base) was added to 8.5 g of each melt and the mixture kept at 140° C. for a further 1-5 minutes. The mixture was then mechanically homogenized and laminated on a pre-warmed sheet (120° C., 250 µm). Pieces of the size desired were cut out.

2.4. Manufacture of an Eva Based Matrix in a Hot Melt Procedure 8.5 g of the EVA hot melt adhesive was heated for around 20 minutes at 160° C. until a homogenous melt was obtained 1.5 g or more precisely 1.65 g high purity fesoterodine base was added as well and the mixture then homogenized manually. The mixture was then laminated on a chill roll brought to a specified temperature (120° C.). In each case 5 cm$^2$ was cut out (for permeation experiments).

3. Releasing Experiments 3.1. Determination of the Flow of Active Ingredient in the Mouse Skin Model Belly and back skin in a thickness of approximately 120 to 150 µm was used for the flux measurements through mouse skin in a horizontal diffusion cell. Medium: phosphate buffer solution (0.066 molar) pH 6.2, 32° C.

Release of the active ingredient was determined by HPLC.

3.2. Determination of the Flow of Active Ingredient in the Human Skin Model (a) Experimental Design The determination of the fesoterodine flux through human skin was essentially performed as described in H. Tanojo et al, J. Control Rel. 45 (1997) 41-47, where instead of the silicone membrane, a dialysis membrane was used [Diachema Dialysemembran, type 10. 14, obtained from the company Dianorm, Munich, Germany, manufactured from neutral cellulose, exclusion size 5000 Da, thickness (dry): 25 µm; pretreatment in accordance with manufacturer information].

Human skin in a thickness of approximately 250 µm was obtained from the abdomen. A TTS with a surface of 2.545 cm$^2$ was applied on a surface similar to human skin, where the skin lay on a silicone membrane acceptor side up. PBS (0.066 molar) was used as the acceptor phase at pH 6.2 and a temperature of 32±0.5° C. The experiments were performed over 72 hours with a 5 mL/hour flux, whereby samples were taken every 3 hours. At the times when the samples are taken the releasing medium is replaced with fresh medium thermo stated at 32±0.5° C. and the amount of the released fesoterodine measured per HPLC.

The determination of the flux rate Q(t) was done based on the area of the measuring cell (0.552 cm$^2$) in compliance with the formula:

Q(t)=µg/cm$^2$=fesoterodine concentration volume of the acceptor/0.552 cm$^2$ (b) Analytical Chemistry of the Release of the Active Ingredient The measurement of the active ingredient flux through the skin preparation is made per HPLC (tower spherisorb 5CN 25 cm) under the following conditions: 4 parts by volume acetonitrile/6 parts by volume H$_2$O/0.1% parts by volume TFA, 35° C., 225 nm, 1 ml flux

4. Analytical Chemistry

Determining the Purity of the Active Ingredient

A HPLC method was used to determine the chemical purity of fesoterodine that is based on the separation at a stationary reversed phase and used for the gradient elution of a solvent. Materials (Exemplary Model):

Acetonitrile for the HPLC, methane sulfonic acid (<99%, Fluka), water (purified, HPCL quality), Waters Pump 510, column heater (Waters Column Heater Module, 35° C.), a sampling device (Waters Wisp 717, injection volume 20 µL), UV-detector (Shimatzu SPD 10A). Column (150×3.9 mm, Symmetry Shield RP8, Waters Part No. WAT 200655).

Mobile Phase:

Acetonitrile with 0.05% methane sulfonic acid (v/v, %), component A

Water with 0.05% methane sulfonic acid (v/v, %), component B

Gradient program: Time (minutes) 0.0 with 15% Component A and 85% Component B, after 15 minutes 60% A and 40% B, after 20 minutes 15% A and 85% B. Flux rate: 1.2 ml/minute The concentrations of the reference solutions of A, B and C (FIG. 1/4, R=i-Pr) amounted to 10-250 µg/mL. Tailing with peak overlap occurred at the higher concentrations.

Analysis:

The average values of all peak surfaces (triple determinations) were added and compared with 100% for analysis according to the 100% method. The areas of the individual peaks were based on this value (as a %). Retention times for A, B and C (minutes): 5.9, 9.0 and 12.6.

5. Analytical Chemistry

Determining the Residual Salt Content

200 MHz or 500 MHz $^1$H-NMR-spectrums of the free base fesoterodine is absorbed in $CDCl_3$ as the solvent and characteristic resonance signal groups are integrated electronically, such as:

δ=6.97 ppm (Duplett, aromatic hydrogen, $H^6$, 1H),
δ=4.59 ppm (Singulett, HO—$CH_2$, 2H),
δ=4.10 ppm (Triplett, $H^1$-Propyl, 1H).

The relation to the resonance signal of the anion, for example, Hydrogen fumarate (δ=6.84 ppm, =CH—, 2H) results in the proportion of residual salt (as a molecular %).

What is claimed is:

1. A pharmaceutical formulation comprising a compound of Formula I,

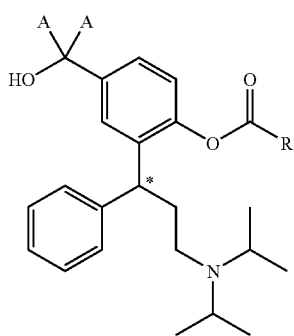

Formula I in which A is deuterium or hydrogen, R is selected from the group consisting of $C_{1-6}$-alkyl, $C_{3-10}$-cycloalkyl and phenyl, which may each be substituted with $C_{1-3}$-alkoxy, fluorine, chlorine, bromine, iodine, nitro, amino, hydroxyl, oxo, mercapto or deuterium and where the C-atom marked with a star "*" may be present in the (R)-configuration, the (S)-configuration or as a mixture of the (R)-configuration and the (S)-configuration, and a pharmaceutically active carrier, wherein the compound of Formula I is present as a free base with a salt content of below 10 wt % and wherein the compound of Formula I is present in a degree of purity of above 97 percent by weight and the pharmaceutical formulation comprises a therapeutically effective amount of the free base of the compound of Formula I.

2. The pharmaceutical formulation according to claim 1, wherein R is selected from the group methyl, ethyl, isopropyl, 1-propyl, 1-butyl, 2-butyl, tertiary-butyl, iso-butyl, pentyl and hexyl.

3. The pharmaceutical formulation according to one claim 1, wherein the compound is 2-[3-(1,1-diisopropylamino)-1-phenylpropyl]-4-(hydroxymethyl)phenyl isobutyrate.

4. The pharmaceutical formulation according to claim 1, wherein the C-atom marked with "*" is present in the (R)-configuration.

5. The pharmaceutical formulation according to claim 1, wherein the compound is (R)-2-[3-(1,1-diisopropylamino)-1-phenylpropyl]-4-(hydroxymethyl)phenyl isobutyrate (fesoterodine).

6. The pharmaceutical formulation according to any one of the claims 1-5, wherein the pharmaceutically acceptable carrier is a polymer.

7. The pharmaceutical formulation according to an one of claims 1-5 having a stabilization factor of at least 2 for the compound of Formula I in the pharmaceutical formulation, wherein the stabilization factor is determined by the division of the average monthly drop in concentration of the compound of Formula I during storage as oil and in the absence of the pharmaceutically acceptable carrier at 5° C. by the average monthly drop in concentration of the corresponding compound of Formula I during storage in the pharmaceutical formulation at 5° C.

8. The pharmaceutical formulation according to claim 7, wherein the formulation exhibits a pH value of 3.0-6.0.

9. The pharmaceutical formulation according to claim 8, wherein the pharmaceutical formulation is suitable for transdermal or transmucosal delivery.

10. The pharmaceutical formulation according to claim 9, wherein the pharmaceutical formulation contains a polymer layer and wherein the compound of Formula I is either dissolved or dispersed in the polymer layer.

11. The pharmaceutical formulation according to claim 10, wherein the polymer layer contains a contact adhesive, which makes the attachment of the pharmaceutical composition to the skin or the mucous membrane of the patient possible.

12. The pharmaceutical formulation according to claim 11, wherein the polymer layer contains a contact adhesive, which makes the attachment of the pharmaceutical composition to the skin of the patient possible and which is chosen from the group consisting of silicone, acrylate, SXS-, PIB- and EVA based contact adhesives.

13. The pharmaceutical formulation according to claim 12, wherein the pharmaceutical formulation is a transdermal therapeutic system of the active ingredient-in-adhesive type.

14. The pharmaceutical formulation according to claim 1, which is a dosing unit that contains at least 3 mg of the compound of Formula I.

15. The pharmaceutical formulation according to claim 5, which is a dosing unit that contains at least 3 mg of (R) 2-[3-(1,1-Diisopropylamino)-1-phenylpropyl]-4-(hydroxymethyl)phenyl isobutyrate (fesoterodine).

16. A kit containing a pharmaceutical formulation according to any one of claims 1 or 5, and a drying agent.

* * * * *